United States Patent
Chen et al.

(10) Patent No.: US 9,415,011 B1
(45) Date of Patent: Aug. 16, 2016

(54) METHOD FOR TREATMENT OF LIVER CANCER AND INHIBITION OF METASTASIS WITH CXC-CHEMOKINE-RECEPTOR 4-TARGETED NANOPARTICLE

(71) Applicant: National Tsing Hua University, Hsinchu (TW)

(72) Inventors: Yun-Ching Chen, Hsinchu (TW); Jia-Yu Liu, Hsinchu (TW); Dong-Yu Gao, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/882,063

(22) Filed: Oct. 13, 2015

(30) Foreign Application Priority Data

Apr. 8, 2015 (TW) .............................. 104111300 A

(51) Int. Cl.
*A61K 8/14* (2006.01)
*A61K 51/12* (2006.01)
*A61K 9/14* (2006.01)
*A61K 31/44* (2006.01)
*A61K 31/7105* (2006.01)

(52) U.S. Cl.
CPC .................. *A61K 9/145* (2013.01); *A61K 31/44* (2013.01); *A61K 31/7105* (2013.01)

(58) Field of Classification Search
CPC .................. A61K 8/14; A61K 9/1271; A61K 2039/55555; A61K 47/48815; A61K 51/12; A61K 9/141; A61K 47/48915; A61K 47/48092; A61L 2300/416
See application file for complete search history.

(56) References Cited

FOREIGN PATENT DOCUMENTS

PT        WO 2014167126        * 10/2014 ............. A61K 47/48

OTHER PUBLICATIONS

Xiang et al. BMC Cancer. 2009:9:176 11 pages.*
Regberg et al. Pharmaceuticals. 2012;5:991-1007.*
Driessen et al. Molecular Therapy. 2008, 16(3): 516-524.*
Lo et al. Molecular Cancer Therapy 2008;7(3):579-89.*
Moradpour et al. (Hepatology 1995;22:1527-1537).*
Dong-Yu Gao et. al., "CXCR4-targeted lipid-coated PLGA nanoparticles deliver sorafenib and overcome acquired drug resistance in liver cancer", Institute of Biomedical Engineering, National Tsing Hua University, Hsinchu, Taiwan, Biomaterials 67 (2015) 194-203.
Jia-Yu Liu et. al., "Delivery of siRNA Using CXCR4-targeted Nanoparticles Modulates Tumor Microenvironment and Achieves a Potent Antitumor Response in Liver Cancer", Molecular Therapy (Aug. 17, 2015), doi: 10.1038/mt.2015.147.

* cited by examiner

*Primary Examiner* — Ernst V Arnold
(74) *Attorney, Agent, or Firm* — WPAT, P.C., Intellectual Property Attorneys; Anthony King

(57) ABSTRACT

Provided is a method for treatment of liver cancer and inhibition of metastasis with CXCR4-targeted nanoparticle. A CXCR4 antagonist is used as a targeting molecule to modify a lipid carrier for the formation of nanoparticle carrying an anti-angiogenesis drug or an anti-angiogenic nucleotide. Such nanoparticle can enhance the accumulation and uptake of the drug and nucleotide in liver cancer cells as well as sensitize the liver cancer cells to treatment of said drug and nucleotide, providing a synergistic suppression of angiogenesis and tumor progression. Furthermore, the CXCR4-targeted nanoparticle can effectively inhibit metastasis of liver cancer. The pharmaceutical composition is an injectable composition; hence, is suitable for clinical application for the treatment of liver cancer.

19 Claims, 40 Drawing Sheets

METHOD FOR TREATMENT OF LIVER CANCER AND INHIBITION OF METASTASIS WITH CXC-CHEMOKINE-RECEPTOR 4-TARGETED NANOPARTICLE

CROSS REFERENCE

This application claims priority of Taiwan Patent Application No. 104111300 filed on 8 Apr. 2015, the content of which is incorporated herein by reference in its entirety.

BACKGROUND OF THE INVENTION

1. Field of the Invention

The present invention relates to a method of using a nanoparticle, and particularly, the present invention relates to a method for treatment of liver cancer and inhibition of metastasis using a CXC-chemokine-receptor 4(CXCR4)-targeted nanoparticle.

2. The Prior Arts

Hepatocellular carcinoma (HCC) is one of the liver primary carcinomas among adults and is also the third most common causes of cancer-related death worldwide. HCC often arises from damaged liver tissues with pre-existing inflammatory microenvironment, fibrosis, and subsequent hypervascularization, and has been identified as a highly vascular tumor. Therefore, anti-angiogenesis therapy has been considered a highly promising therapeutic strategy for treatment of HCC. Currently, tyrosine kinase inhibitor such as sorafenib is widely used since it suppresses angiogenesis and tumor progression by blocking VEGFR/PDGFR in the tumor vasculature and the RAF/MEK/ERK pathway in HCC cells. Sorafenib is by far the only approved drug for systematic treatment of advanced HCC and can effectively promote the overall survival of patients.

However, the use of sorafenib produces certain side-effects, such as hand-foot syndrome, diarrhea, and hypertension, due to oral administration and its non-specific uptake by normal tissues. Furthermore, due to poor solubility in water, the absorption of sorafenib in the gastrointestinal tract is low, which leads to unfavorable pharmacokinetics. Some studies have shown that HCCs can rapidly evade from anti-angiogenesis therapy and become resistant to sorafenib, resulting in high incidence of HCC recurrence locally and at distant sites. Thus, there are still many difficulties regarding effective anti-angiogenesis therapy for treatment of HCC including the occurrence of drug resistance and the considerable toxicity thereof.

Moreover, some researches indicated that prolonged treatment of sorafenib may decrease neovasculature and increase tumor hypoxia. In hepatocellular carcinoma, a variety of hypoxia-induced gene expression changes involving in genomic instability, angiogenesis and metastasis contribute to tumor progression and sorafenib resistance in HCC. The sorafenib-induced hypoxia increases the expression of CXC-chemokine-receptor 4(CXCR4) and stromal cell-derived factor 1α(SDF1α). SDF1α/CXCR4 axis plays an important role in regulating tumor growth, angiogenesis, invasion and recruitment of tumor-promoting stroma cells. AMD3100, a cationic bicyclam molecule, blocks SDF1α/CXCR4 axis and sensitizes HCC to sorafenib treatment by inhibiting SDF1α/CXCR4 axis-induced cancer cell proliferation and polarization of tumor-promoting microenvironment. However, AMD3100 also exhibits poor pharmacokinetics and high unwanted toxicity which make the combination approach of sorafenib and AMD3100 difficult to be applied in patients with HCC.

SUMMARY OF THE INVENTION

Accordingly, the present invention provides a method for treatment of liver cancer and inhibition of metastasis of liver cancer, comprising administrating to a subject in need a therapeutically effective amount of a pharmaceutical composition comprising a CXC-chemokine-receptor 4(CXCR4)-targeted nanoparticle, the nanoparticle comprises: a core, comprising an anti-angiogenesis drug or a nucleotide having an anti-angiogenic effect; a lipid carrier for encapsulating the core; and a CXCR4-targeted molecule attached to the surface of the lipid carrier, wherein the CXCR4-targeted molecule specifically delivers the nanoparticle to a hepatocellular carcinoma and enhances the inhibitory effect of the anti-angiogenesis drug or the nucleotide having an anti-angiogenic effect in the hepatocellular carcinoma. The lipid carrier further comprises a polymer and the polymer is poly [D, L-lactide-co-glycolide] (PLGA). The nanoparticle of the present invention can further comprises a stabilizer or an emulsifier. The stabilizer can be, for example, 1,2-distearoyl-sn-glycero-3-phosphoethanolamine-N-[amino(polyethylene glycol)-2000] (DSPE-PEG (2000)), while the emulsifier can be, for example, D-α-Tocopherol polyethylene glycol 1000 succinate (TPGS). The pharmaceutical composition of the present invention is, preferably, an injection.

In one embodiment of the present invention, the nanoparticle of the present invention decreases the viability of the hepatocellular carcinoma while enhances the accumulation of the anti-angiogenesis drug or the nucleotide having an anti-angiogenic effect in the hepatocellular carcinoma. In another embodiment of the present invention, the nanoparticle of the present invention decreases the density and diameter of a new vessel of the hepatocellular carcinoma. The anti-angiogenesis drug is, preferably, sorafenib; the nucleotide having an anti-angiogenic effect is, preferably, a small interfering RNA (siRNA). The CXCR4-targeted molecule is, preferably, a CXCR4 anatognist, and more preferably, AMD3100. In still another embodiment of the present invention, the AMD3100 increases the sensitivity of the hepatocellular carcinoma to the anti-angiogenesis drug and the nucleotide having an anti-angiogenic effect.

The present invention is further explained in the following embodiment illustration and examples. Those examples below should not, however, be considered to limit the scope of the invention, and it is contemplated that modifications will readily occur to those skilled in the art, which modifications will be within the spirit of the invention and scope of the appended claims.

DETAILED DESCRIPTION OF THE PREFERRED EMBODIMENT

Figure 1A:
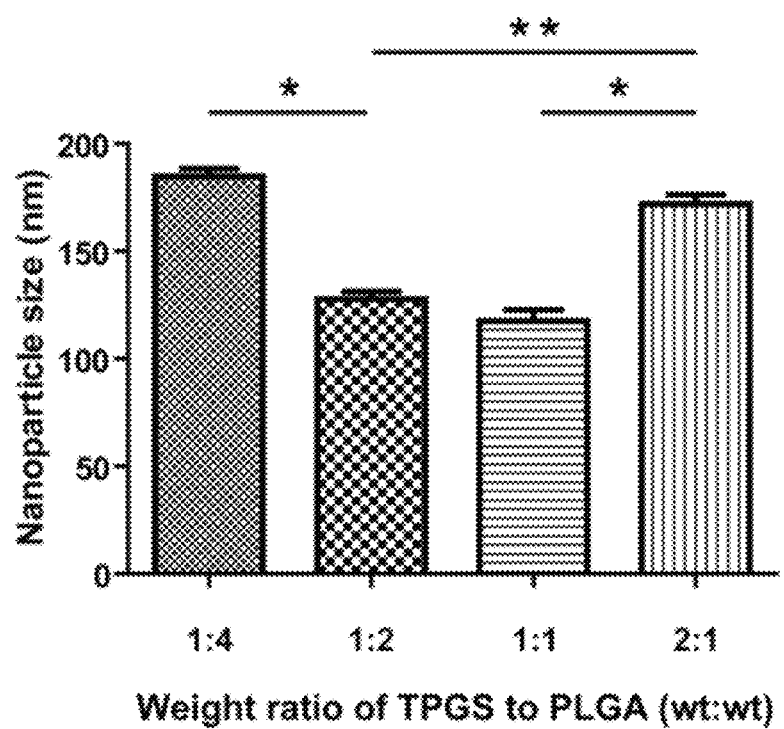
FIG. 1A, the sizes of the nanoparticles formed with different weight ratios of TPGS:PLGA (wt:wt).

The present invention provides a method for treatment of liver cancer and inhibition of metastasis. Firstly, CXCR4-targeted nanoparticles containing an anti-angiogenesis drug or a nucleotide having an anti-angiogenic effect were prepared. The nanoparticle is constituted of a core, a lipid carrier, and a CXCR4-targeted molecule. Characteristics such as size, zeta-potential, polydispersity index (PDI), and pharmacokinetics were analyzed. Then, in vivo and in vitro absorption of the CXCR4-targeted nanoparticles containing an anti-angiogenesis drug or a nucleotide having an anti-angiogenic effect and cytoxicity to hepatocellular carcinoma were evaluated. According to experimentations, the CXCR4-targeted nanoparticle of the present invention can not only enhance the accumulation and uptake of the materials encapsulated therein, but also increase the sensitivity of hepatocellular carcinoma to chemotherapy agents. On the other hand, encapsulation of an anti-angiogenesis drug (ie. Sorafenib) or a nucleotide having an anti-angiogenic effect (ie. Anti-VEGF siRNA) can be beneficial regarding inhibition of angiogenesis, metastasis, and tumor progression of hepatocellular carcinoma. Hence, the method for treatment of liver cancer and inhibition of metastasis of the present invention is able to achieve specific delivery of drug or therapeutic molecule to the target cells while promoting the synergistic anti-cancer effect of said drug or therapeutic molecule. In addition, the method of the present invention shows a potent inhibitory effect against highly malignant cancer and can be formulated into an injection without undesired side-effects. As a result, the present invention is useful and applicable for treatment and clinical application of cancers, particularly hepatocellular carcinoma.

Materials and Methods

Materials

D-α-Tocopherol polyethylene glycol 1000 succinate (TPGS), coumarin 6 (C6), Protamine sulfate salt (from salmon), calf thymus DNA, anti-VEGF siRNA with sequence 5'-AUGUGAAUGCAGACCAAAGAA-3', and control siRNA with sequence 5'-AATTCTCCGAACGTGTCACGT-3' were purchased from Sigma-Aldrich (St. Louis, Mo.). Methanol was purchased from Alfa Aesar (Ward Hill, Mass.). Sorafenib was purchased from LC laboratories (Boston, USA) or Bayer Schering Pharma (Berlin, Germany), whereas AMD3100.8HCl was purchased from Selleckchem (Houston, USA) or Sigma-Aldrich (St. Louis, Mo.). 1,2-dioleoyl-sn-glycero-3-phosphate (sodium salt) (DOPA), 1,2-Dioleoyl-sn-glycero-3-phosphocholine (DOPC), cholesterol, and 1,2-distearoyl-sn-glycero-3-phosphoethanolamine-N-[amino (polyethylene glycol)-2000 (DSPE-PEG (2000)) was purchased from AvantiPolar Lipids (Alabaster, Ala.). Poly [D, L-lactide-co-glycolide] (PLGA, 50:50, inherent viscosity: 0.17 dl/g) were purchased from Green Square Materials Incorporation (Taoyuan, Taiwan). Ethylenediaminetetraacetic acid (EDTA) was purchased from Merck (Alabaster, Ala.). For cellular and tumor uptake studies, FAM was conjugated to the 5' end of the sense sequence. 5'-FAM-labeled VEGF siRNA was purchased from MDBio, Inc. (Taipei, Taiwan). Recombinant SDF-1α was purchased from ProSpec Techno-Gene (Rehovot, Israel).

Cell Culture

For the preferred embodiments of the present invention, murine hepatocellular carcinoma cell line HCA-1 and human hepatocellular carcinoma cell line JHH-7 were used. HCA-1 and JHH-7 cell lines were cultured in suspension in Dulbecco's modified Eagle's medium (DMEM)/high glucose and Dulbecco's modified Eagle medium/nutrient mixture F-12 (Hyclone, Logan, Utah), respectively, while supplemented with 10% FBS (Hyclone, Logan, Utah) and 5% antibiotics of penicillin and streptomycin (Hyclone, Logan, Utah) at 37° C. in an incubator (Forma 370, Thermo Fisher Scientific, USA) with the atmosphere of 5% $CO_2$. For in vitro and in vivo experimentations, HCA-1 and JHH-7 cells were cultured until the cell confluence reached 75% or above.

Animals 4 to 6-week-old male C3H/HeNCrNarl mice (weight: 25 g) were purchased from National Laboratory Animal Center (Taipei, Taiwan). In order to create hepatocellular carcinoma model, every mouse was orthotopically injected with HCA-1 cells ($10^6$ cells per mouse) in liver.

Example 1

Preparation and Formulation of the Anti-Angiogenesis Drug-Loaded CXCR4-Targeted Nanoparticle For the present invention, a sorafenib-loaded AMD3100-modified DOPA-PLGA nanoparticle was provided and such nanoparticle was synthesized via a single-step nanoprecipitation. Briefly, materials including PLGA, sorafenib, TPGS and DOPA were dissolved in DMSO as stock solutions with concentrations of 75, 30, 100 and 4 mg/mL, respectively. The weight percentage of sorafenib to PLGA was fixed at 20%. Particular amounts of PLGA, sorafenib, TPGS and DOPA in DMSO were mixed to form an oil phase. Then, the oil phase was added to the water phase dropwise under gentle stirring. The nanoparticles were allowed to self-assemble in 30 minutes with continuous stirring at room temperature. The volume of oil to water phase was fixed to the ratio of 1:7 (v/v). After stirring, the suspension was collected and added with the specific amount of AMD3100. For purification, the solution was centrifuged at 16,200 rpm for 30 min at 25° C. to collect the nanoparticles and then the nanoparticles were resuspended in the water or PBS (Hyclone, Logan, Utah) for storage purpose.

The same procedure set forth above was used to synthesize sorafenib-loaded nanoparticles corresponding to the different ratio of PLGA to TPGS, DOPA or AMD3100. Also, the synthesis of coumarin 6-loaded nanoparticle was based on the above procedure except that sorafenib was replaced by coumarin 6.

Sorafenib were encapsulated into a PLGA nanoparticle and an anionic lipid DOPA and TPGS were used to stabilize the structure of such nanoparticle. Firstly, the influence of TPGS—an emulsifier—content on the core structure of nanoparticle was examined. The results indicated that there was a decrease in particle size (from 175 nm to 125 nm) when the weight ratio of TPGS to PLGA in the oil phase was increased from 1/4 to 4/4 (w/w) while the concentration of PLGA remained constant (FIG. 1A). It was noted that an increase in particle size (from 125 nm to 170 nm) was observed when the weight ratio of TPGS to PLGA reached 2/1. Therefore, the particle size decreases with increasing TPGS concentration. However, when concentration of TPGS exceeded a certain level, it resulted in an increased size of the nanoparticle, suggesting that an insufficient amount of emulsifier led to unstabilized nanoparticles and aggregation. In other words, the stabilization effect of the emulsifier toward PLGA nanoparticle no longer exists when the emulsifier concentration is above a sufficient amount.

Figure 1B:
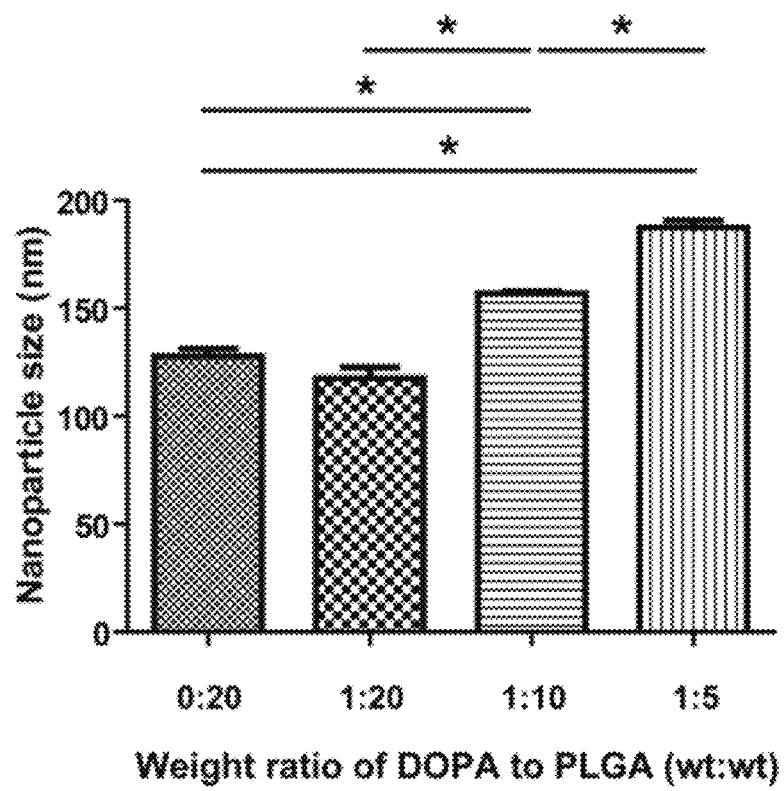
FIG. 1B, the sizes of the nanoparticles formed with different weight ratios of DOPA:PLGA (wt:wt).
Figure 1C:
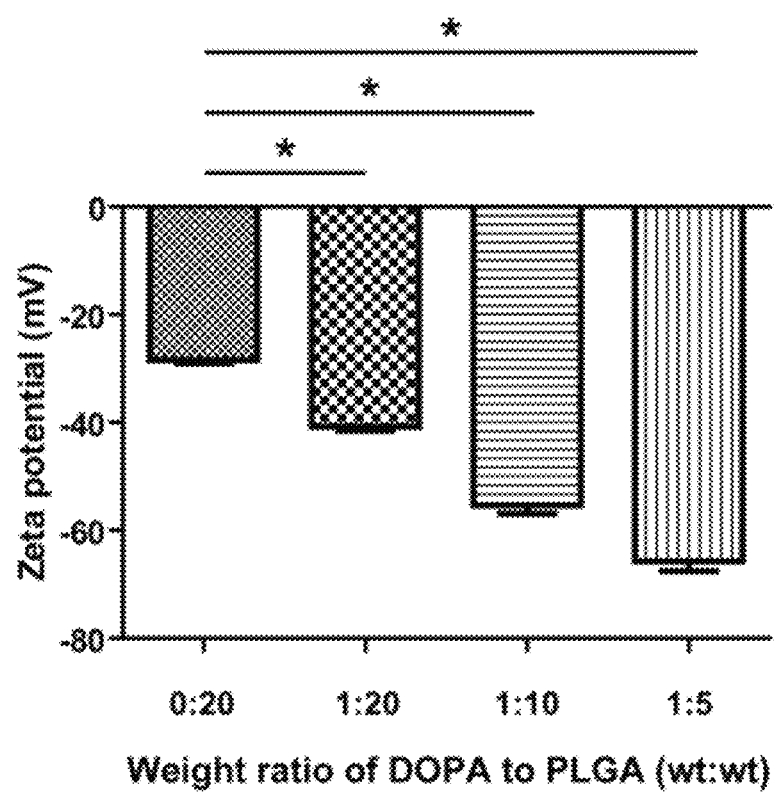
FIG. 1C, the zeta-potential of the nanoparticles formed with different weight ratios of DOPA:PLGA (wt:wt).

Next, the effect of the anionic lipid DOPA coated on the surface of PLGA nanoparticle was examined. As shown in FIG. 1B, there was no significant difference in particle size when a small amount of DOPA was added (weight ratio of DOPA to PLGA=1/20). However, when the weight ratio of DOPA to PLGA was further increased from 1/20 to 4/20, the particle size increased, approximately, from 118 nm to 187 nm. Furthermore, the sorafenib-loaded DOPA-PLGA nanoparticle without AMD3100 modification (DOPSor) exhibited a strong negative surface charge (FIG. 1C).

Figure 1D:
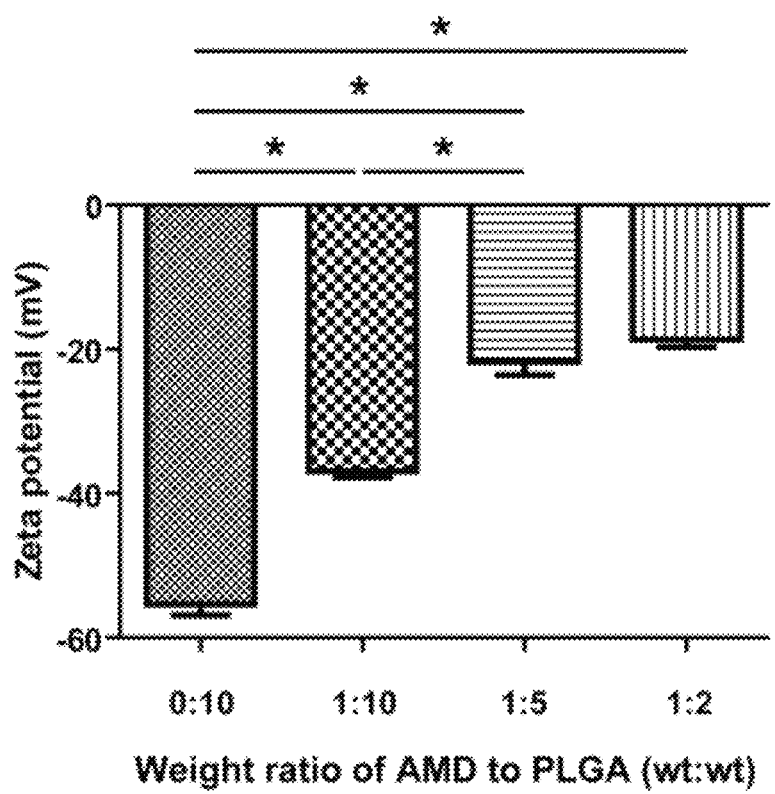
FIG. 1D, the zeta-potential of the nanoparticles formed with different weight ratios of AMD3100:PLGA (wt:wt).

Then, in an attempt to achieve tumor targeting as well as to overcome acquired resistance for sorafenib treatment, AMD3100, a ligand of CXCR4 with positive charges was added into the negative charged surface of DOPSor by charge-charge interaction. The result showed that an increased amount of AMD3100 coated on DOPSor led to an increased surface charge of the nanoparticle. There was an increase in surface charge (from −55 mV to −19 mV) when the weight ratio of AMD3100 to PLGA was increased from 0/20 to 10/20 (w/w) (FIG. 1D). Hence, through adjusting parameters including TPGF to PLGA, lipid to PLGA and ADM3100 to PLGA, the nanoparticles of the present invention can be synthesized with desired size and charge. Preferably, a weight ratio of 2:1:5:10:2 (AMD3100/DOPA/TPGS/PLGA/Sorafenib) was used for the preparation of an anti-angiogenesis drug-loaded CXCR4-targeted lipid-coated PLGA nanoparticle, for example, the sorafenib-loaded AMD3100-modified DOPA-PLGA nanoparticle of the present invention (ADOPSor).

Example 2

Characterization of the Anti-Angiogenesis Drug-Loaded CXCR4-Targeted Nanoparticle The size and morphology of ADOPSor nanoparticles of the present invention were examined by a transmission electron microscopy (TEM) (H-7500, HITACHI, from Chang Gung memorial hospital, Taoyuan). The ADOPSor nanoparticles of the present invention were firstly stained on dried carbon-stabilized Formvar-coated 200-mesh copper grids (Ted Pella, Inc., Redding, USA) at room temperature. Then, all grids were freshly dried for two days prior to imaging.

The particle size and surface charge were measured by Zetasizer (3000HS, Malvern Instruments Ltd., Worcestershire, UK) at room temperature after the nanoparticles were centrifuged twice by collecting the supernatant first and then resuspending pellet after samples underwent the high-speed centrifugation. The parameters of viscosity and refraction index were set equal to water for all samples during testing.

The geometries and size distribution of DOPSor and ADOPSor were analyzed by a transmission electron microscopy. Both DOPSor and ADOPSor were well-dispersed spheres with sizes around 195 nm, which were consistent with the particle sizes detected by DLS. The average diameters of the DOPSor and ADOPSor determined by DLS were 156.98±0.95 nm and 175.25±1.82 nm, with polydispersity indexes (PDIs) of 0.136±0.007 and 0.148±0.004, respectively.

Example 3

Preparation and Formulation of the CXCR4-Targeted Nanoparticle Encapsulating a Nucleotide Having an Anti-Angiogenic Effect The present invention also provides a CXCR4-targeted nanoparticle encapsulating a nucleotide having an anti-angiogenic effect. Briefly, anionic liposomes composed of DOPA, DOPC and cholesterol (1:2:1 molar ratio) were prepared by thin film hydration followed by sonication (Q125, Qsonica, USA) at 50 W for 2 minutes on ice to reduce the particle size. To prepare the core of the nanoparticle, a mixture of 18 μL AMD3100 (2 mg/mL), 16 μL of protamine (2 mg/mL), 120 μL of deionized water, and 22 μL of a mixture of siRNA (12 μL, 3 mg/mL) and calf thymus DNA (10 μL, 2 mg/mL) were mixed and kept at room temperature for 5 minutes before 90 μL of anionic liposomes (20 mmol/L) were added. After mixing the anionic liposomes with the DNA-Protamine-AMD3100 cores, the mixture solution stood at room temperature for 10 minutes. Then, for attaching AMD3100 onto the nanoparticle, the solution was then mixed with AMD3100 in PBS and kept at room temperature for 5 minutes. Finally, the solution was further mixed with 20 μL of DSPE-PEG (10 mg/mL), a stabilizer, and kept at 55° C. for 10 minutes to form the siRNA-loaded AMD3100-modified nanoparticle.

Example 4

Characterization of the Preferred CXCR4-Targeted Nanoparticle Loaded with a Nucleotide Having an Anti-Angiogenic Effect For the nanoparticle obtained via the procedure set forth above in Example 3, the average size of the protamine/DNA complex therein was 169.8 nm and the zeta potential thereof was −28.6 mV. When AMD3100 was added to the protamine/nucleic acids complex, the particle size reduced to 110.7 nm and the zeta potential became positive (27 mV). On the other hand, the average size of the nanoparticle with the protamine/nucleic acids/AMD3100 complex within an anionic liposome composed of DOPC, DOPA and cholesterol was 1133 nm and it was negatively charged (−52.9 mV).

To achieve tumor targeting, the surface of the above anionic liposome-coated nanoparticles was further coated with a CXCR4 ligand, AMD3100, resulting in a nanoparticle with less negative charges (−23.4 mV) compared to the nanoparticle without AMD3100 modification. Finally, such AMD3100-modified nanoparticle was attached with DSPE-PEG to prolong its systemic circulation in the blood. The TEM images indicated that the siRNA-loaded AMD3100-modified nanoparticle of the present invention was spherical with an average diameter of 144.7±14 nm and a PDI of 0.299±0.03.

Example 5

In Vitro Cellular Uptake of the CXCR4-Targeted Lipid-Coated PLGA Nanoparticle

For evaluating the in vitro cellular uptake of the CXCR4-targeted lipid-coated PLGA nanoparticle of the present invention, firstly, HCA-1 or JHH-7 cells were seeded in the 12-well transparent plate with coverglasses (Costar, Ill., USA) at a density of $10^5$ cells/well in medium and were incubated for 12 hours. Then, C6-loaded lipid-coated PLGA nanoparticle (DOPC6) and C6-loaded AMD3100-modified lipid-coated PLGA nanoparticle (ADOP-C6) as indicated above were added into the medium and incubated for 4 hours. The final C6 concentrations for HCA-1 and JHH-7 cells were 6.42 μM and 3.21 μM, respectively. After incubation, the suspension in wells was removed and wells were washed with PBS. After washing, cells were fixed with 4% paraformaldehyde and mildly shaken for 10 minutes, and then washed with PBS again. The coverglasses were then mounted on the slide with mounting solution (4',6-diamidino-2-phenylindole, DAPI) in order to counterstain nuclei. The cell uptake of C6 was examined and calculated by confocal laser scanning microscope (LSM-780, Carl Zeiss, Germany) at the wavelength of 603 nm.

On the other hand, for the AMD3100 competitive cellular uptake assay, cells were prepared according to the procedure mentioned above. Free AMD3100 was added into medium at the final concentration of 0 µM, 0.2 µM, 2 µM and 20 µM for 10 minutes and C6-loaded AMD3100-modified lipid-coated PLGA nanoparticle were then added into the medium at the same concentration to examine the effect of AMD3100-CXCR4 internalization. Cells were incubated for 4 hours and the cell uptake of C6 was examined and calculated by confocal laser scanning microscope as indicated above.

Figure 2A:
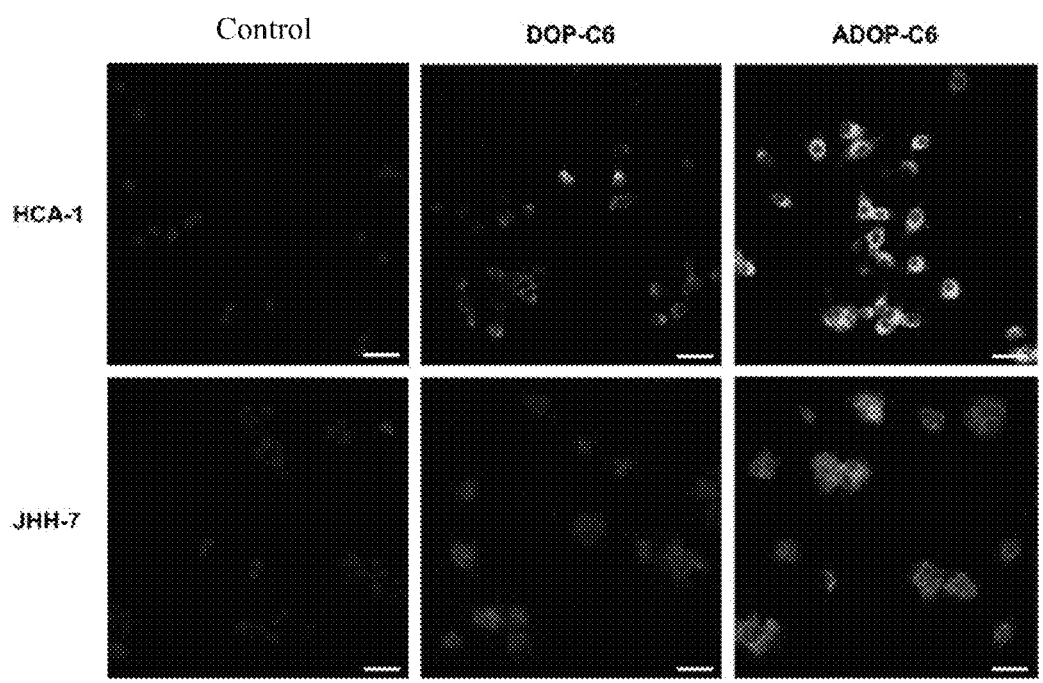
FIG. 2A, the fluorescence microscopy images of the HCA-1 cells and JHH-7 cells treated with C6 (Coumarin 6)-loaded AMD3100-modified lipid-coated PLGA nanoparticle (ADOP-C6) or C6-loaded lipid-coated PLGA nanoparticle (DOP-C6) for 4 hours.
Figure 2B:
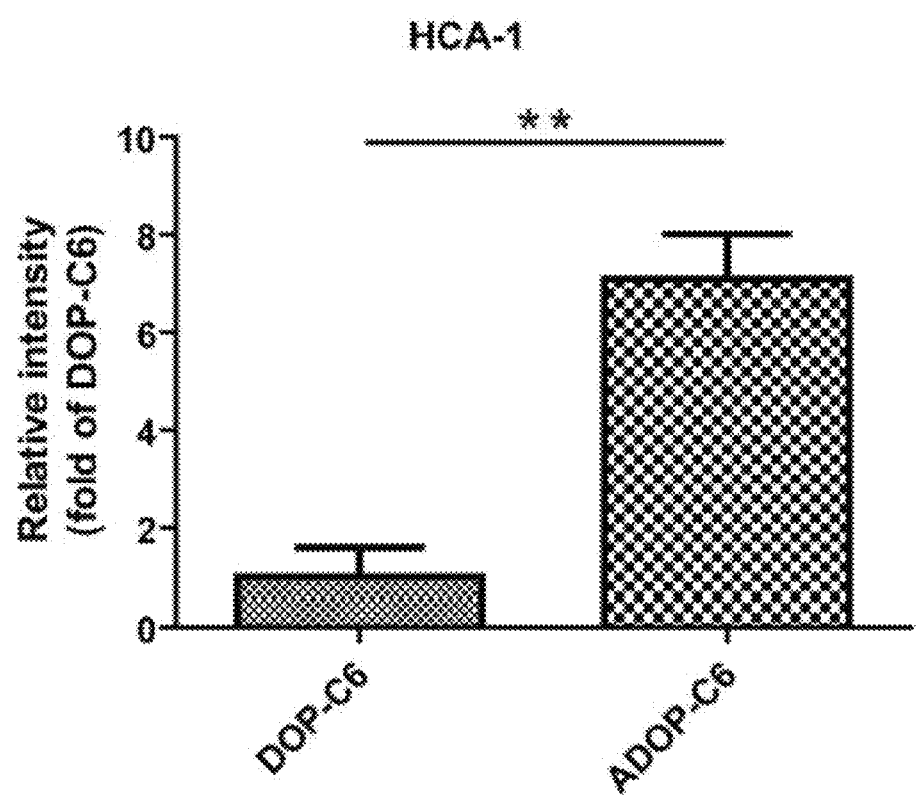
FIG. 2B, the relative fluorescent intensities of ADOP-C6 or DOP-C6 localized at HCA-1 cells, indicating the absorption of the nanoparticle of the present invention by the HCA-1 cells.
Figure 2C:
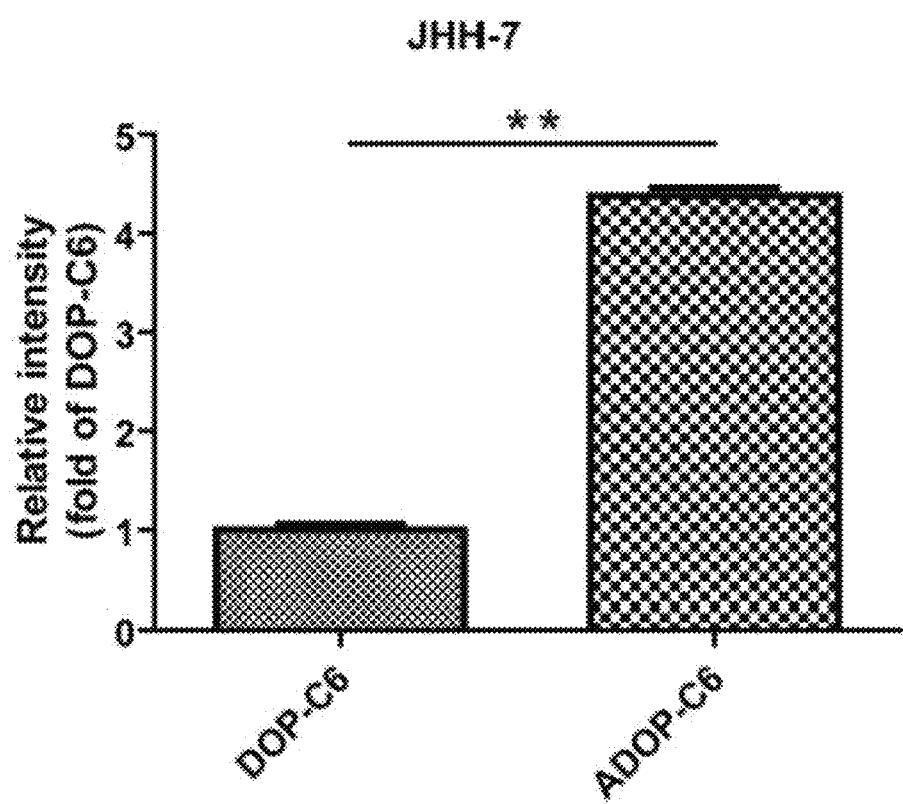
FIG. 2C, the relative fluorescent intensities of ADOP-C6 or DOP-C6 localized at JHH-7 cells, indicating the absorption of the nanoparticle of the present invention by the JHH-7 cells.
Figure 2D:
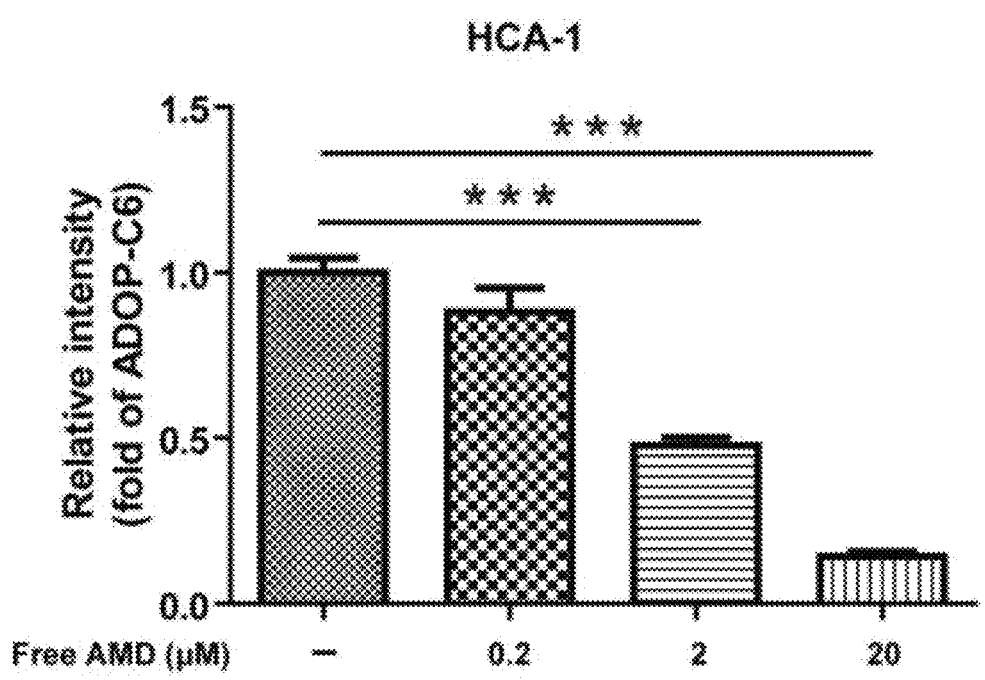
FIG. 2D, the relative fluorescent intensities of ADOP-C6 localized at HCA-1 cells in the absence or presence of free AMD3100, indicating the competitive effect of AMD3100 against the absorption of the nanoparticle.

To measure the in vitro uptake of CXCR4-targeted nanoparticles in hepatocellular carcinoma, C6 was used as a tracer molecule and formulated in AMD3100-modified DOPA-PLGA nanoparticle (ADOPC6) or DOPA-PLGA nanoparticle without AMD3100 modification (DOP-C6). The final weight ratio of C6 to PLGA was 1/150. As shown in FIG. 2A to FIG. 2C, the uptake of C6 was greater in both HCA-1 and JHH-7 cell treated with ADOP-C6 than those treated with DOP-C6. Furthermore, the uptake of ADOP-C6 was competitively inhibited by addition of free AMD3100 in a dose-dependent manner (FIG. 2D), indicating that the cellular uptake of ADOP-C6 is ligand (AMD3100) specific.

Example 6

In Vitro Cytotoxicity of the CXCR4-Targeted Lipid-Coated PLGA Nanoparticle

For cytotoxicity examination of the CXCR4-targeted lipid-coated PLGA nanoparticle of the present invention, HCA-1 or JHH-7 cells were seeded in 96-well transparent plates (Costar, Ill., USA) at a density of 1000 cells/well in a medium and were incubated for 12 hours. After confluency reached 10%, the medium was replaced with RPMI-1640 media containing DOPSor, ADOPSor, free DOPA, ADOP, or DOPSor with free AMD3100 at the equivalent sorafenib concentration of 0.25 µM. Concerning the treatment of free drug, cells in 96-well plate were treated with RPMI-1640 medium containing free AMD3100, free sorafenib, or free AMD3100 plus free sorafenib, at sorafenib concentration of 0.25 µM and AMD3100 concentration of 0.2 µM. All cells were incubated for 48 hours. After incubation for another 3 hours, MTT assay was utilized to subsequently measure the cell viability. The absorbance of the wells was measured by Multiskan (Thermo, USA) at 570 nm and background absorbance was subtracted from all data. The percentage of cell viability was calculated by normalization of all values to the control group.

Figure 3A:
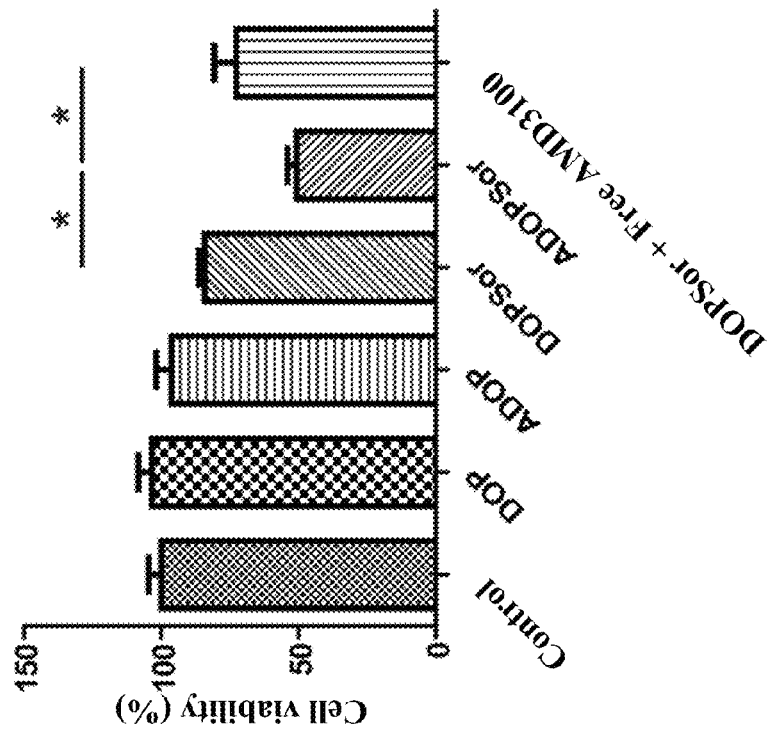
FIG. 3A, the cell viability of the HCA-1 cells treated with the CXCR4-targeted lipid-coated PLGA nanoparticle of the present invention, wherein the control group is the HCA-1 cells left untreated.
Figure 3A:
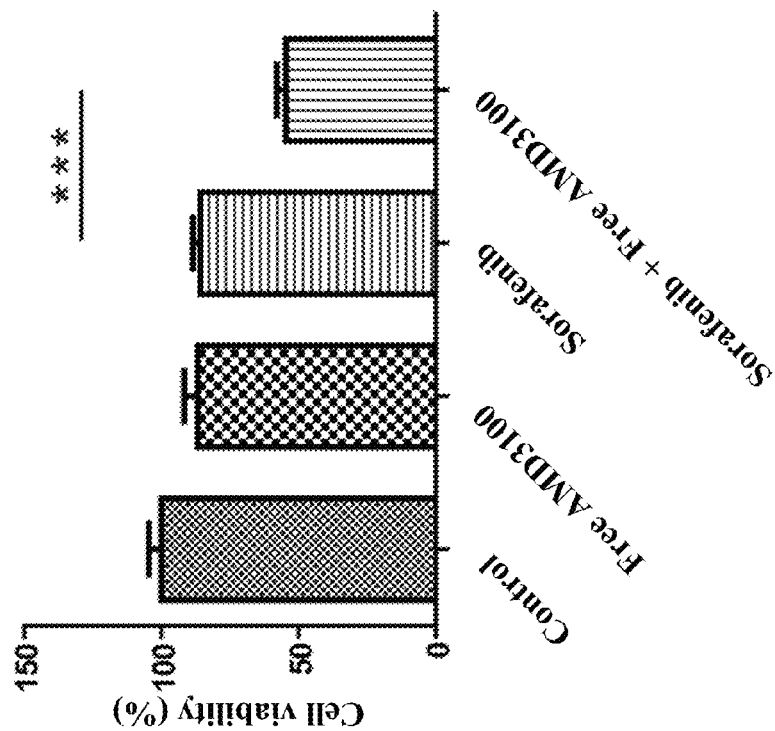
Figure 3B:
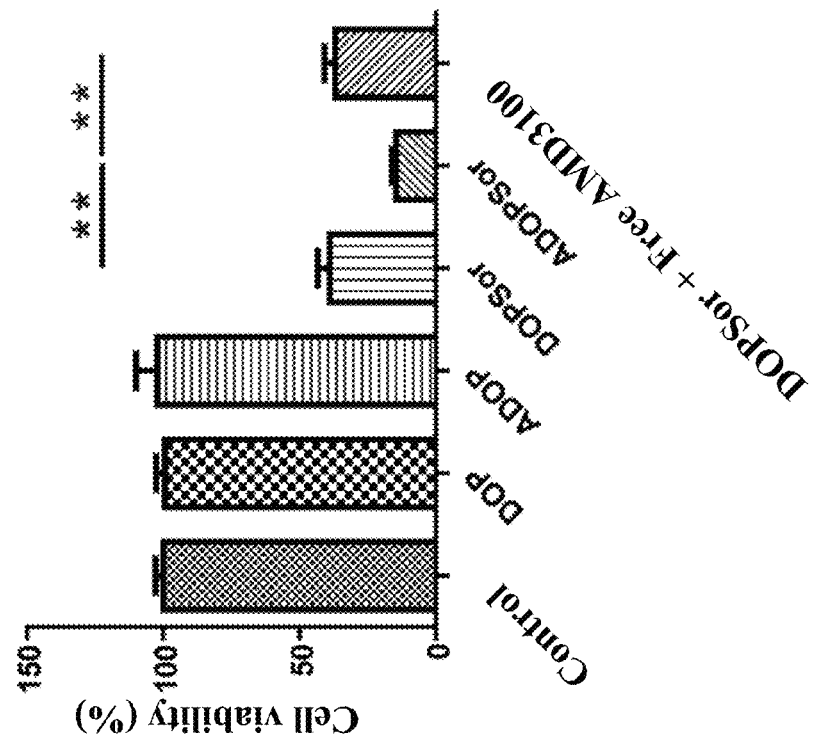
FIG. 3B, the cell viability of the JHH-7 cells treated with the CXCR4-targeted lipid-coated PLGA nanoparticle of the present invention, wherein the control group is the JHH-7 cells left untreated.
Figure 3B:
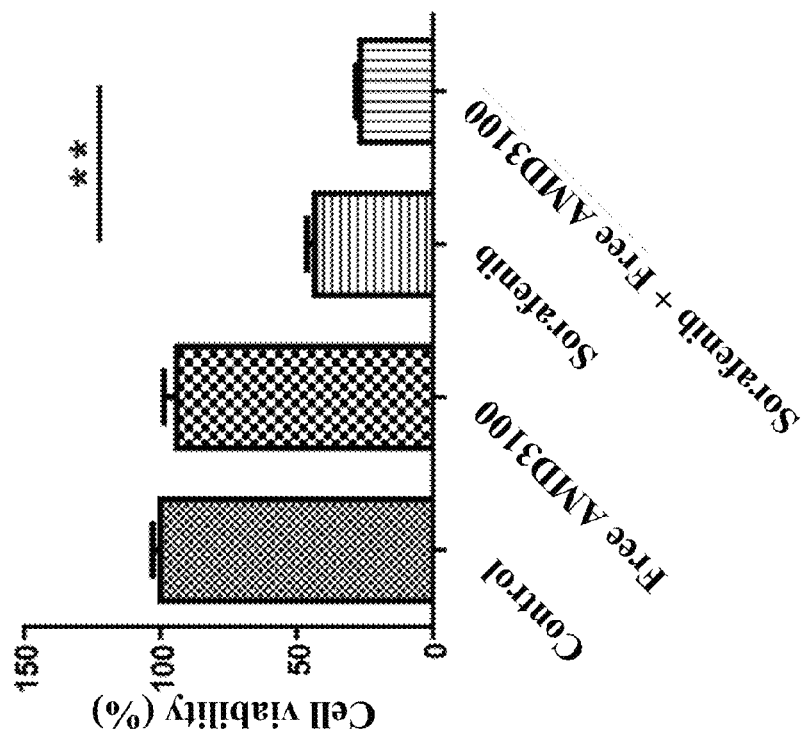

HCA-1 cells or JHH-7 cells without any treatment were defined as the control group. The result of in vitro cytotoxicity indicated that treatment with AMD3100 alone did not have a cytotoxic effect on both HCA-1 and JHH-7 cells (FIG. 3A and FIG. 3B, left panels). However, AMD3100 slightly sensitized HCC to sorafenib treatment. The cytotoxicity of the sorafenib-loaded lipid-coated PLGA nanoparticles with or without AMD3100-modification (ADOPSor and DOPSor) was further examined. The cytotoxicity was higher in both HCA-1 and JHH-7 cell lines treated with ADOPSor (FIG. 3A and FIG. 3B, right panels) when compared to cells treated with DOPSor. The blank nanoparticles (DOP and ADOP) showed no significant cytotoxicity in both HCA-1 and JHH-7 cell lines. It was noted that, similar to the result shown in FIG. 3A and FIG. 3B, left panels, free AMD3100 slightly sensitized HCC to DOPSor. However, treatment with ADOPSor still displayed more significant cell death when compared with treatment with free AMD3100 plus DOPSor. These results demonstrated a synergistic cytotoxic effect when AMD3100 was attached to the sorafenib-loaded nanoparticle. Thus, it is proven that AMD3100 can be used both as a targeting ligand to deliver the cargoes into HCC and a sensitizer to chemotherapeutic drugs such as sorafenib.

Example 7

In Vivo Pharmacokinetics of the CXCR4-Targeted Lipid-Coated PLGA Nanoparticle

To examine the pharmacokinetics profile in vivo, firstly, C6-loaded lipid-coated PLGA nanoparticle without AMD3100 modification (DOP-C6) and C6-loaded AMD3100-modified lipid-coated PLGA nanoparticle (ADOP-C6) were prepared according to the method set forth above. Then, C3H mice with orthotopic HCA-1 tumor were administered with free C6, DOP-C6 and ADOP-C6 at a dosage of 2 mg/kg. 40 µl of blood was collected from the tail artery and mixed with 10 µL of EDTA (50 mM) at different periods of time. The fluorescence intensity was measured by the plate reader (Fluoroskan Ascent FL, Thermo Scientific) at an excitation wavelength of 485 nm and an emission wavelength of 538 nm C6 concentration was normalized and calculated from a standard curve obtained by spiking known amounts of free C6 or C6-loaded nanoparticles in blood obtained from uninjected mice.

Figure 4A:
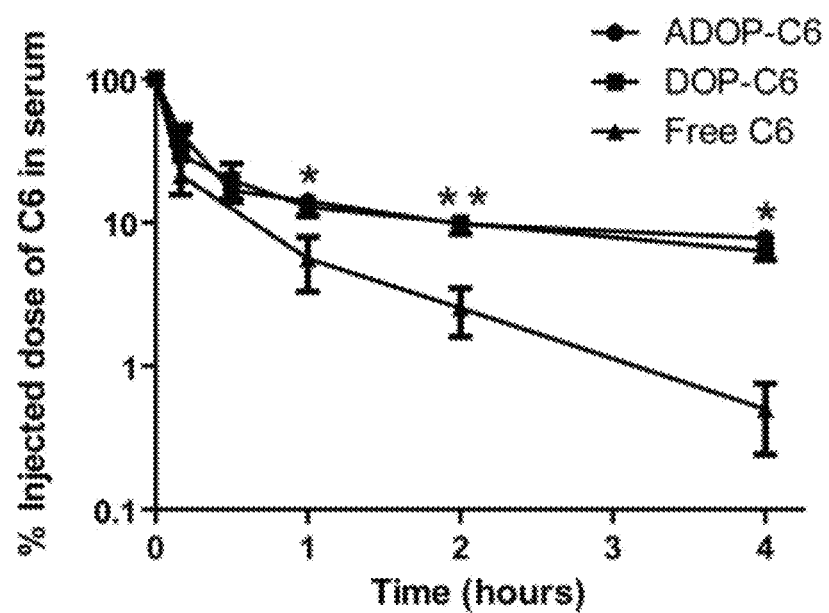
FIG. 4A, in vivo pharmacokinetics of the CXCR4-targeted lipid-coated PLGA nanoparticle of the present invention.

As shown in FIG. 4A, free C6 was cleared rapidly from the blood after 1 hour and was almost cleared out after 4 hours of injection. However, C6-loaded nanoparticles (DOP-C6 and ADOP-C6) remained in blood after 1 hour of injection and then maintained steadily at about 10% in circulation even after 4 hours, suggesting that either DOP-C6 or ADOP-C6 can significantly prolong circulation of C6 in vivo compared with the free C6.

Example 8

In Vivo Liver Uptake of the CXCR4-Targeted Lipid-Coated PLGA Nanoparticle

Figure 4B:
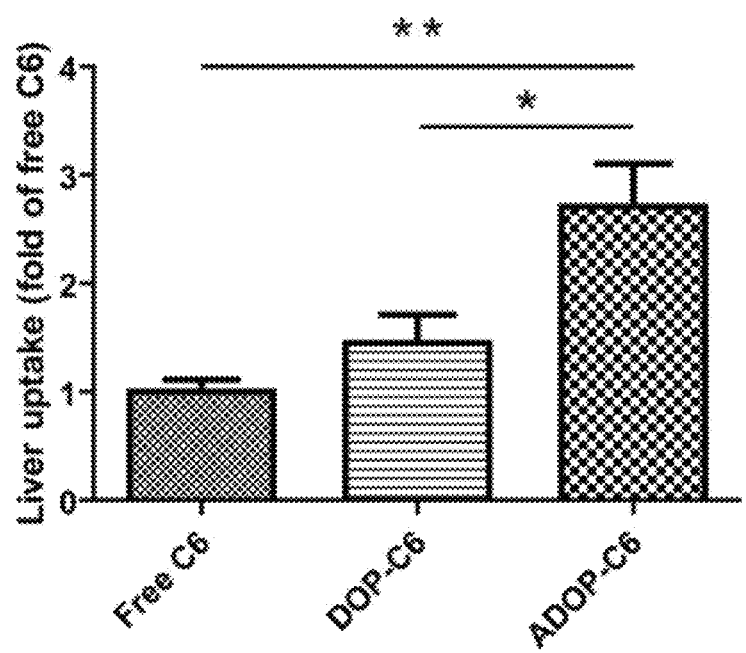
FIG. 4B, in vivo liver accumulation of the CXCR4-targeted lipid-coated PLGA nanoparticle of the present invention.
Figure 4C:
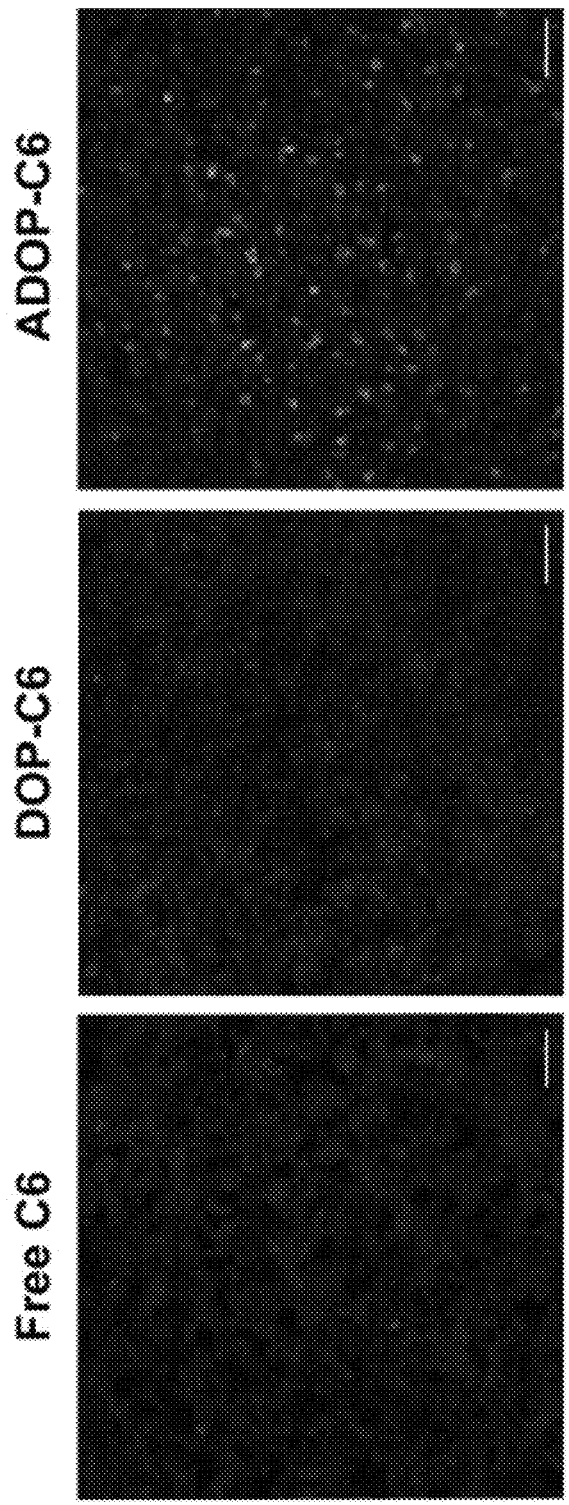
FIG. 4C, the fluorescence microscopy images of the in vivo liver accumulation of the CXCR4-targeted lipid-coated PLGA nanoparticle of the present invention.

C3H mice with orthotopic HCA-1 tumor were injected with free C6, DOP-C6, and ADOP-C6 as described in Example 7. After 4 hours, all mice were sacrificed and livers were obtained for the examination of C6 accumulation. The accumulation of free C6 and C6-loaded nanoparticles in the orthotopic HCA-1 livers was examined and calculated by the confocal microscope. As shown in FIG. 4B and FIG. 4C, the accumulation of C6 in the orthotopic HCA-1 liver was significantly greater in mice treated with ADOP-C6 than mice treated with free C6. On the other hand, no significant difference in hepatic uptake between the DOP-C6 and free C6 was observed, indicating that CXCR4-targeted lipid-coated PLGA nanoparticles can enhance the uptake and accumulation in liver.

Example 9

AMD3100-Modified Nanoparticle Modulates the Tumor Microenvironment and Sensitize HCC to Sorafenib Treatment In Vitro and In Vivo To examine cell viability, cells without any treatment were defined as Negative control group, while cells treated with free sorafenib alone were defined as Positive control group. Meanwhile, cells treated with sorafenib in the presence of recombinant SDF1α were defined as Comparative group 1, while cells treated with free sorafenib and free AMD3100 were defined as Comparative group 2. Regarding the experimental groups, cells treated with sorafenib-loaded lipid-coated nanoparticle without AMD3100 modification were defined as Experimental group 1, while cells treated with sorafenib-loaded AMD3100-modified lipid-coated nanoparticle were defined as Experimental group 2.

Figure 5A:
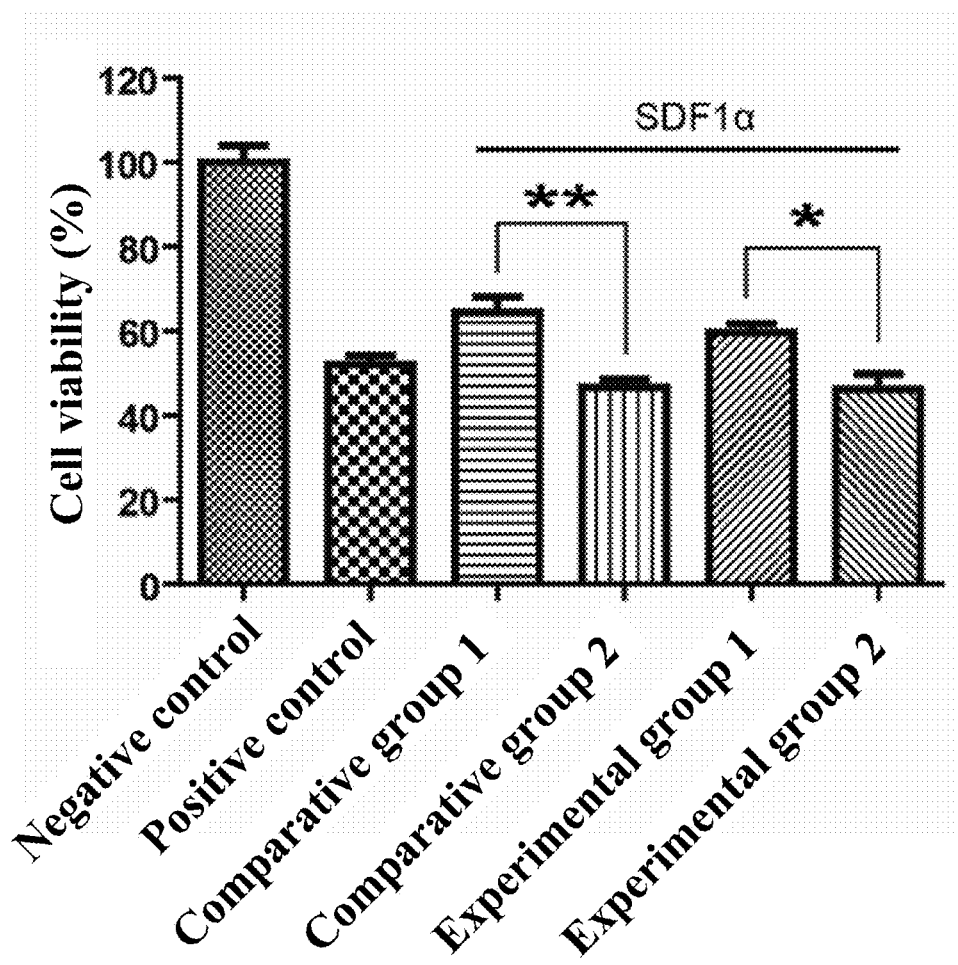
FIG. 5A, the cell viability of the JHH-7 cells treated with the siRNA-loaded CXCR4-targeted lipid-coated nanoparticle of the present invention, $*p<0.05$; $**p<0.01$.
Figure 5B:
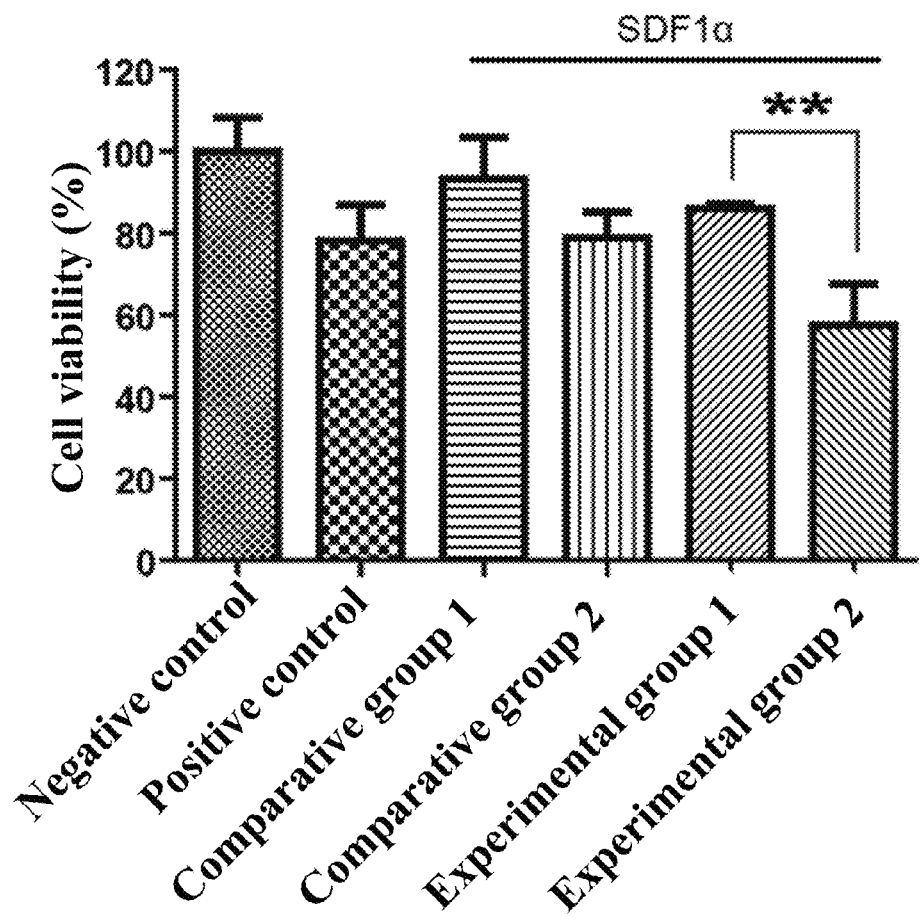
FIG. 5B, the cell viability of the HCA-1 cells treated with the siRNA-loaded CXCR4-targeted lipid-coated nanoparticle of the present invention, $**p<0.01$.

To determine whether the SDF1α/CXCR4 axis mediates HCC resistance to sorafenib treatment, both murine HCC (HCA-1) and human HCC (JHH-7) cell lines were firstly exposed to recombinant SDF1α in the presence of sorafenib. As shown in FIG. 5A and FIG. 5B, SDF1α increased the viability of both JHH-7 and HCA-1 cells despite sorafenib treatment (Experimental group 1 and Comparative group 1). Furthermore, Experimental group 2 showed that the inhibition of CXCR4 by AMD3100 prevented the effects of SDF1α and sensitized HCC to sorafenib treatment.

On the other hand, HCA-1 cells were intrahepatic ally implanted into C3H mice to establish a syngeneic orthotopic murine HCC model. For evaluation of mean vessel density (MVD) and hypoxic induction, mice without any treatment were defined as Negative control group, while mice treated with free sorafenib alone were defined as Positive control group. Mice treated with free sorafenib and free AMD3100 were defined as Comparative. For the experimental groups, mice treated with AMD3100-modified lipid-coated nanoparticle of the present invention were defined as Experimental group 1, while mice treated with sorafenib and AMD3100-modified lipid-coated nanoparticle of the present invention together were defined as Experimental group 2.

Figure 6A:
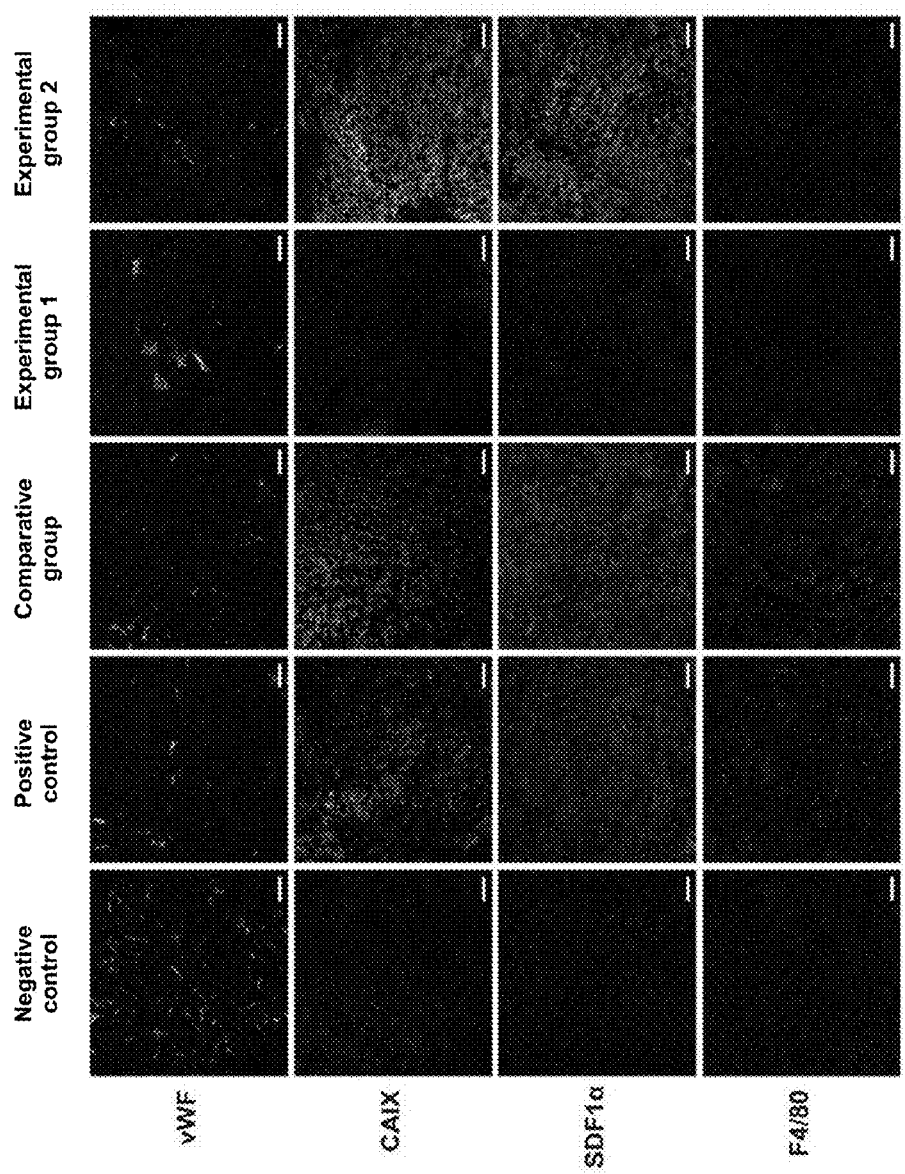
FIG. 6A, the fluorescence microscopy images of the mice with orthotopic HCA-1 tumor treated with sorafenib and the AMD3100-modified lipid-coated nanoparticle of the present invention, the scale therein represents 50 µm.
Figure 6B:
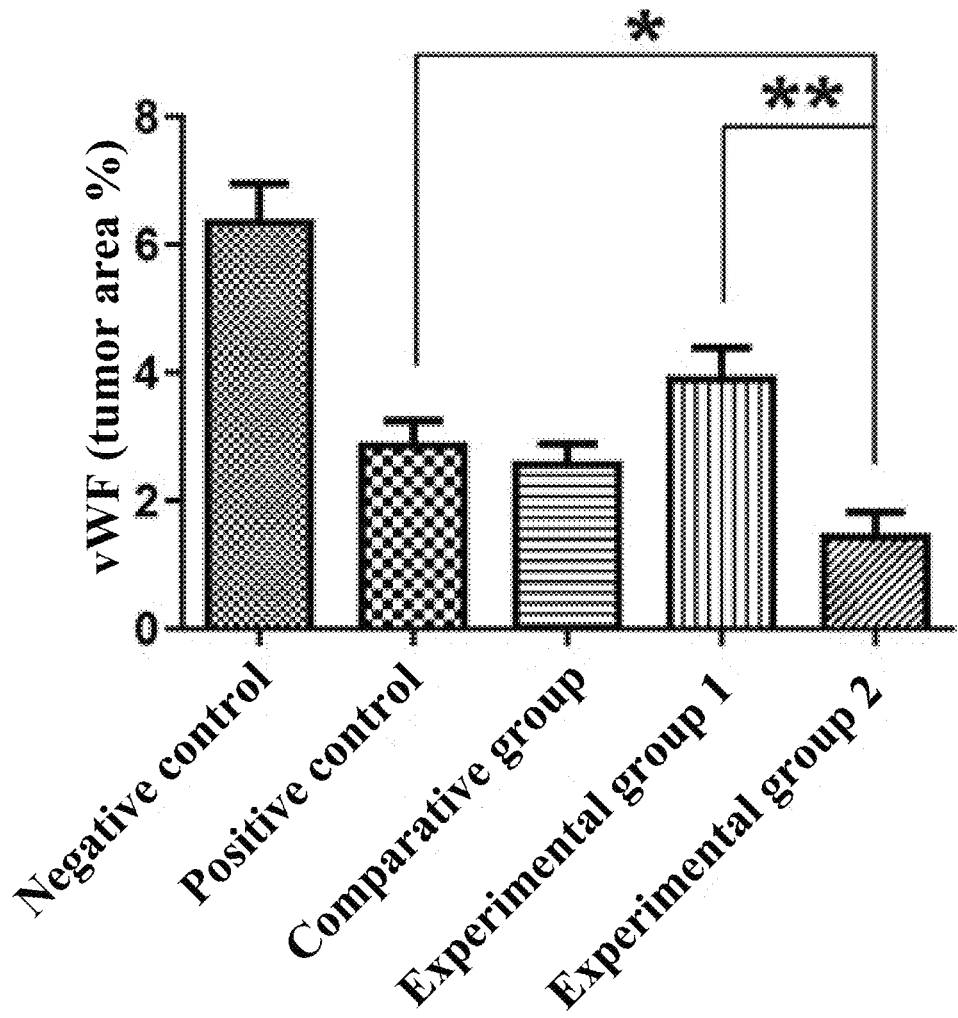
FIG. 6B, the quantification of the fluorescence microscopy images of von Willebrand factor (vWF) expression in mice with orthotopic HCA-1 tumor treated with sorafenib and the AMD3100-modified lipid-coated nanoparticle of the present invention, $*p<0.05$; $**p<0.01$.
Figure 6C:
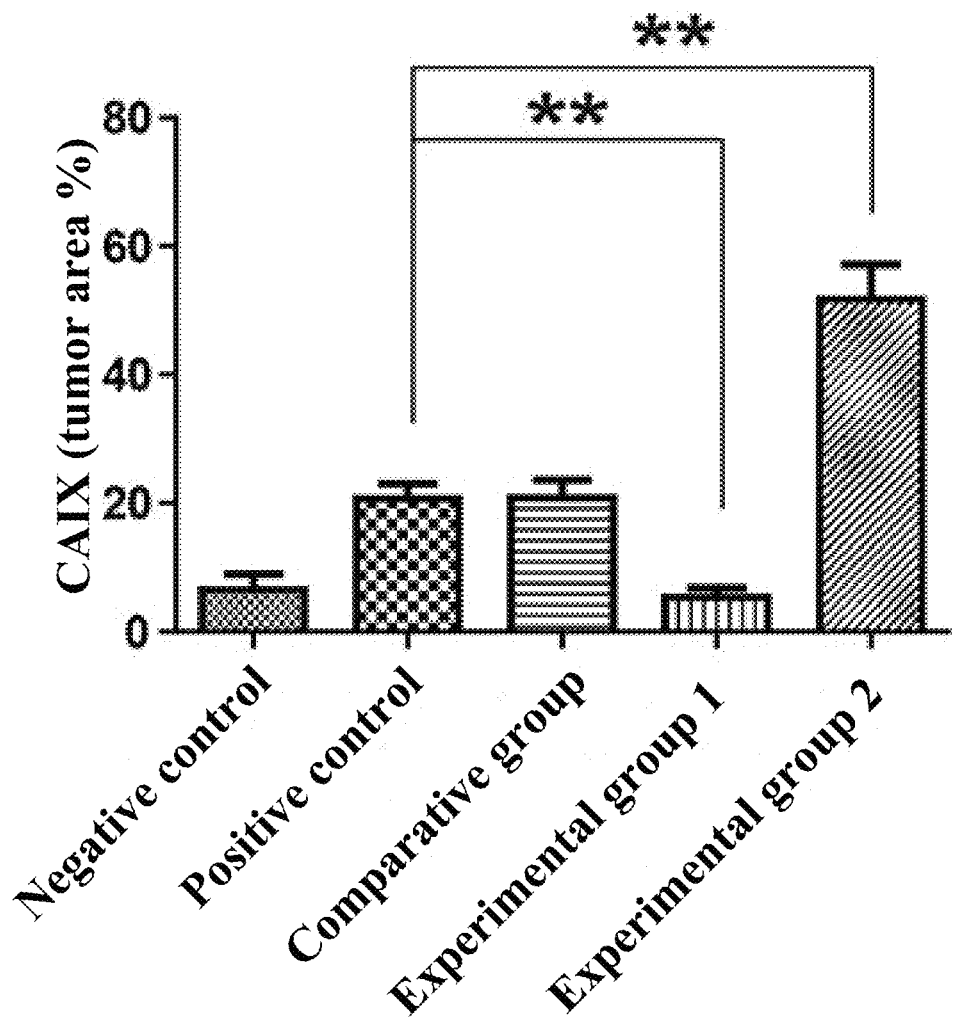
FIG. 6C, the quantification of the fluorescence microscopy images of carbonic anhydrase IX (CAIX) expression in mice with orthotopic HCA-1 tumor treated with sorafenib and the AMD3100-modified lipid-coated nanoparticle of the present invention, $**p<0.01$.
Figure 6D:
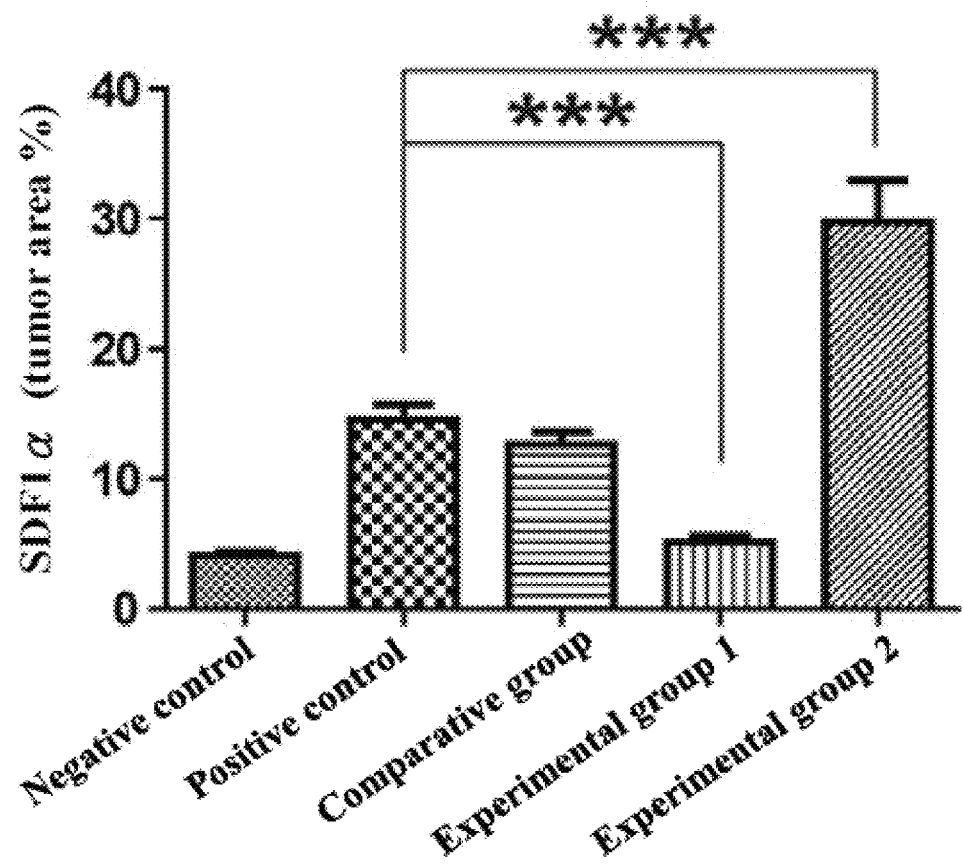
FIG. 6D, the quantification of the fluorescence microscopy images of stromal derived factor 1α (SDF1α) expression in mice with orthotopic HCA-1 tumor treated with sorafenib and the AMD3100-modified lipid-coated nanoparticle of the present invention, $***p<0.001$.

After HCC tumors were established, mice were treated according to the above mentioned Positive control group, Comparative group, Experimental group 1, and Experimental group 2 with sorafenib given at a dose of 50 mg/kg daily for 14 days. Regarding the changes in MVD and tissue hypoxia of the implanted tumor tissues, Positive control group showed significant reduction of MVD and increase of carbonic anhydrase IX (CAIX) expression, indicating hypoxia induction (FIG. 6A to FIG. 6C). On the other hand, the change in SDF1α expression as a consequence of treatment-induced hypoxia was examined. The result showed that a 3-fold increase in SDF1α expression in HCA-1 tumor tissues in Positive control group (FIG. 6A and FIG. 6D).

Figure 6E:
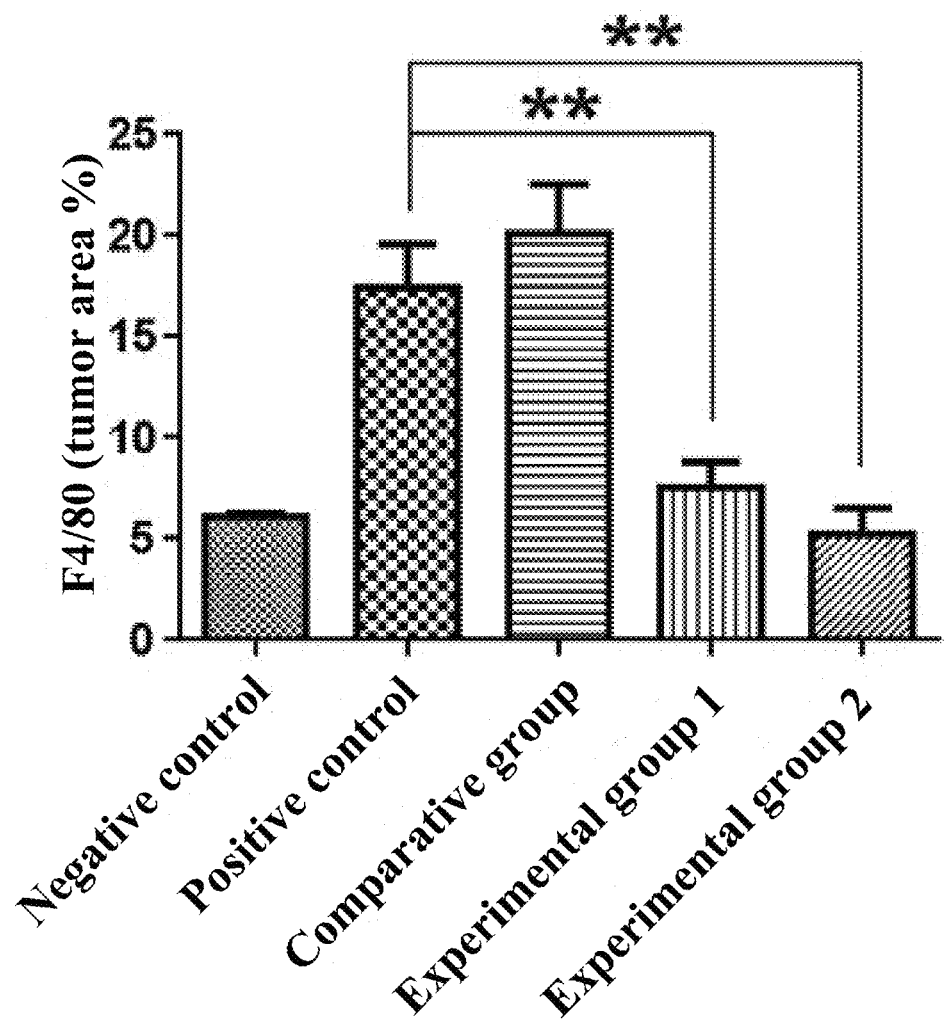
FIG. 6E, the quantification of the fluorescence microscopy images of tumor-associated macrophage F4/80 in mice with orthotopic HCA-1 tumor treated with sorafenib and the AMD3100-modified lipid-coated nanoparticle of the present invention, $**p<0.01$.

Next, the effect of inflammatory cell infiltration in HCC was examined. The results showed that, in the orthotopic murine HCA-1 model, the number of F4/80+ macrophages increased by over 3-fold in Positive control group (FIG. 6A to FIG. 6E), whereas, in Experimental group 1 and Experimental group 2, the number of tumor-infiltrating F4/80+ macrophages was decreased to a level similar to the Negative control group (FIG. 6A to FIG. 6E) due to blocking of SDF1α/CXCR4 axis. However, as shown in FIG. 6E, due to poor pharmacokinetics, the addition of free AMD3100 to the sorafenib treatment (Comparative group) did not show significant differences compared to sorafenib treatment alone (Positive control group). Since tumor-associated macrophages (TAMs) play a key role in regulating the tumor microenvironment toward pro-angiogenesis and metastasis, the use of AMD3100-modified lipid-coated nanoparticle in combination with sorafenib for inhibition of tumor-associated macrophages can synergistically suppress angiogenesis, metastasis and tumor progression.

Figure 7A:
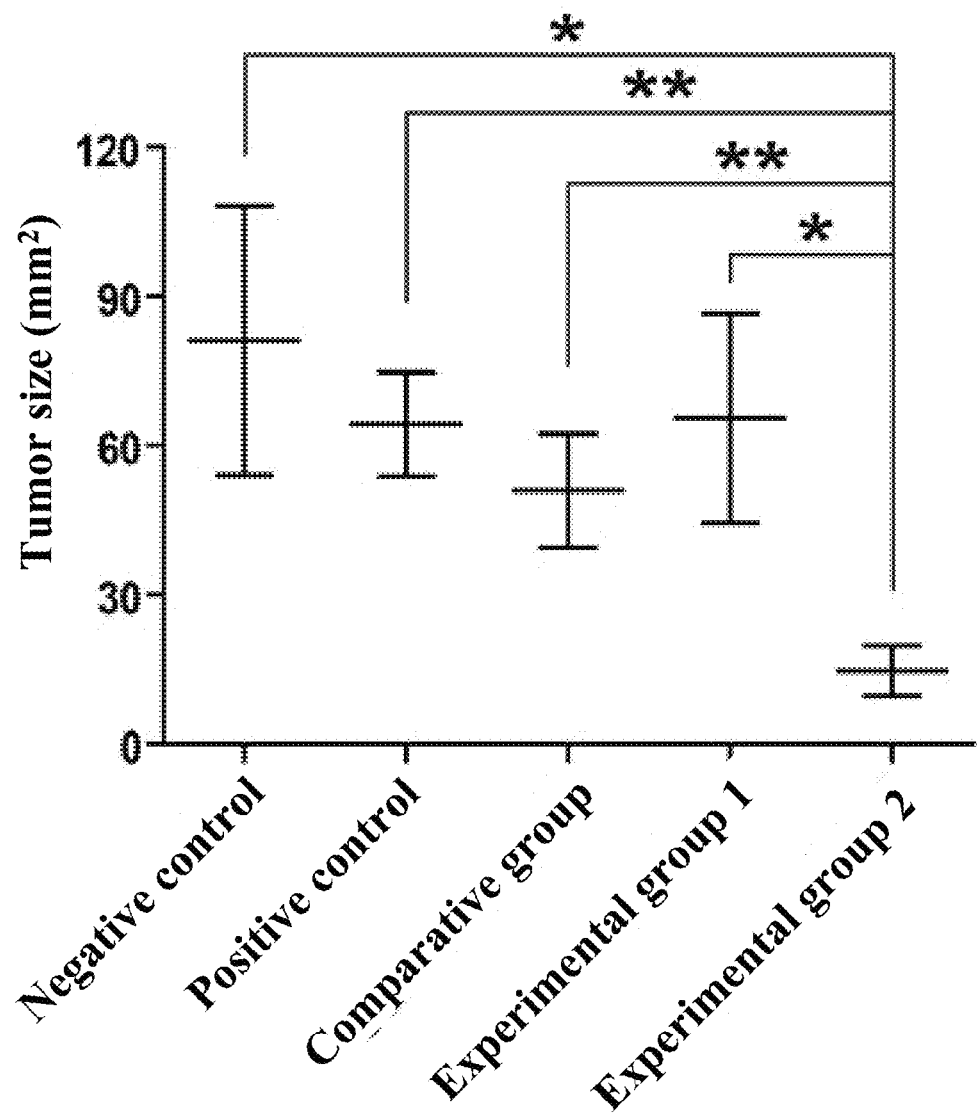
FIG. 7A, the tumor sizes of the mice with orthotopic HCA-1 tumor treated with sorafenib and the AMD3100-modified lipid-coated nanoparticle of the present invention, $*p<0.05$; $**p<0.01$.
Figure 7B:
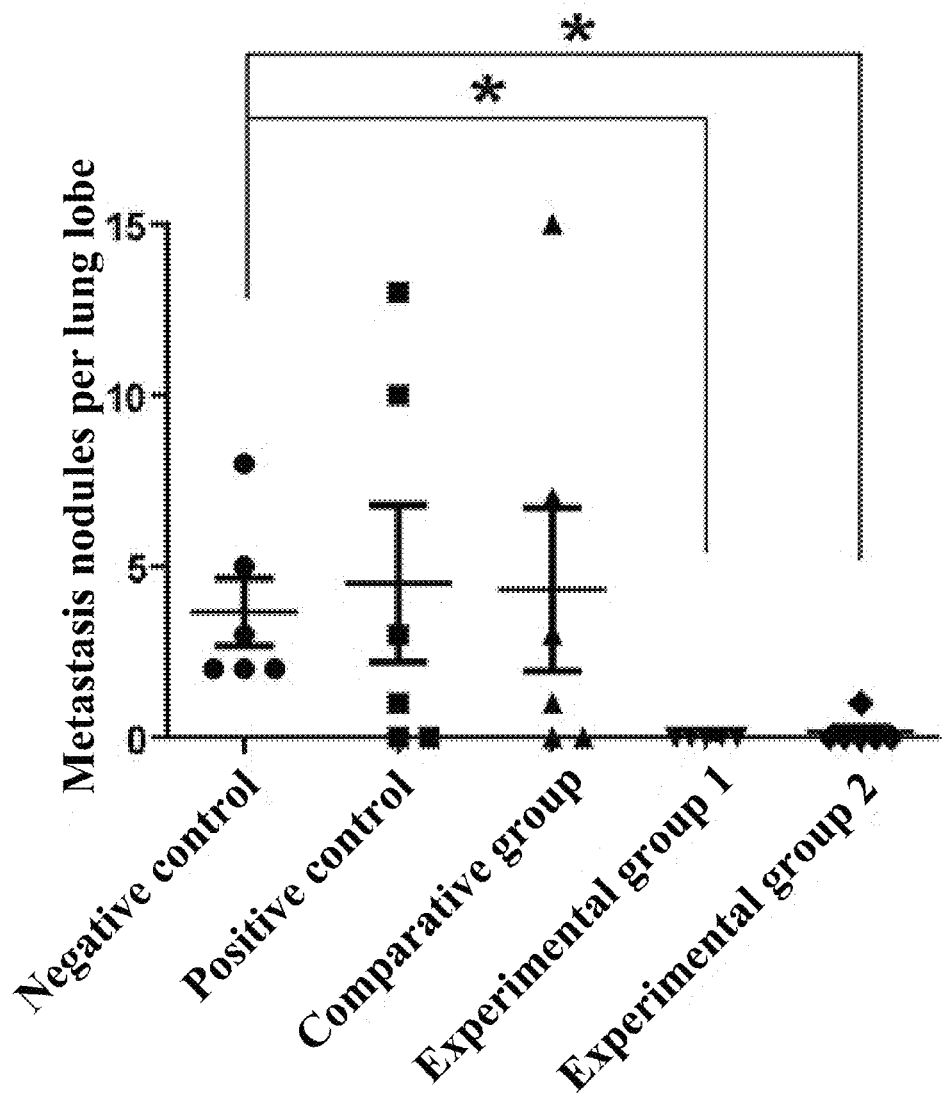
FIG. 7B, the lung metastasis of the mice with orthotopic HCA-1 tumor treated with sorafenib and the AMD3100-modified lipid-coated nanoparticle of the present invention, $*p<0.05$.
Figure 7C:
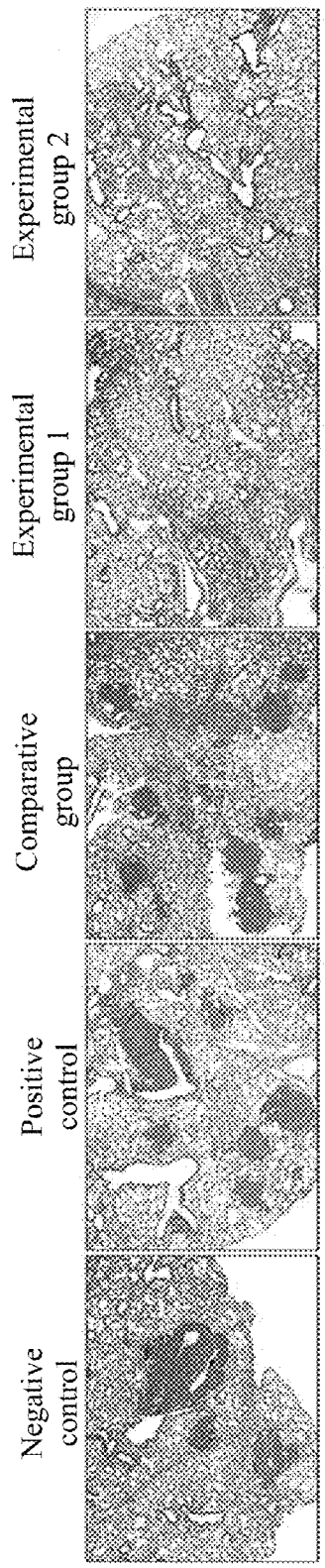
FIG. 7C, the microscopic images of the lung metastasis of the mice with orthotopic HCA-1 tumor treated with sorafenib and the AMD3100-modified lipid-coated nanoparticle of the present invention.

Furthermore, the effect of HCC progression in HCA-1 transplanted mice model was evaluated. As shown in FIG. 7A, the Positive control group exhibited a moderate tumor growth inhibitory effect. Due to poor pharmacokinetics of free AMD3100, the systemic injection of free AMD3100 (Comparative group) did not significantly sensitize HCC to sorafenib treatment in vivo. However, according to Experimental groups, the systemic administration of AMD3100-modified nanoparticles in combination with sorafenib led to the synergistic tumor growth inhibition of orthotopic HCA-1 tumors in C3H mice. In the HCA-1 orthotopic mice model, spontaneous lung metastases developed around day 14 after tumor implantation. Neither the Positive control group nor the Comparative group showed a reduction in metastasis formation (FIG. 7B to FIG. 7C). In contrast, the Experimental group 1 and the Experimental group 2 showed significant inhibition of lung metastasis in the orthotopic HCA-1 mice model (FIG. 7B to FIG. 7C). These results indicated that the SDF1α/CXCR4 pathway can regulate metastasis and the AMD3100-modified nanoparticle can block CXCR4, resulting in efficient reduction of metastasis.

Example 10

Delivery of Anti-VEGF siRNA Using AMD3100-Modified Nanoparticle Shows Significant Gene Silencing in HCC In Vitro and In Vivo Firstly, cells treated with free control siRNA were defined as Control group, while cells treated with free anti-VEGF siRNA were defined as Comparative group. Cells treated with anti-VEGF siRNA-loaded lipid-coated nanoparticle without AMD3100 modification were defined as Experimental group 1, while cells treated with anti-VEGF siRNA-loaded AMD3100-modified lipid-coated nanoparticle were defined as Experimental group 2.

Figure 8A:
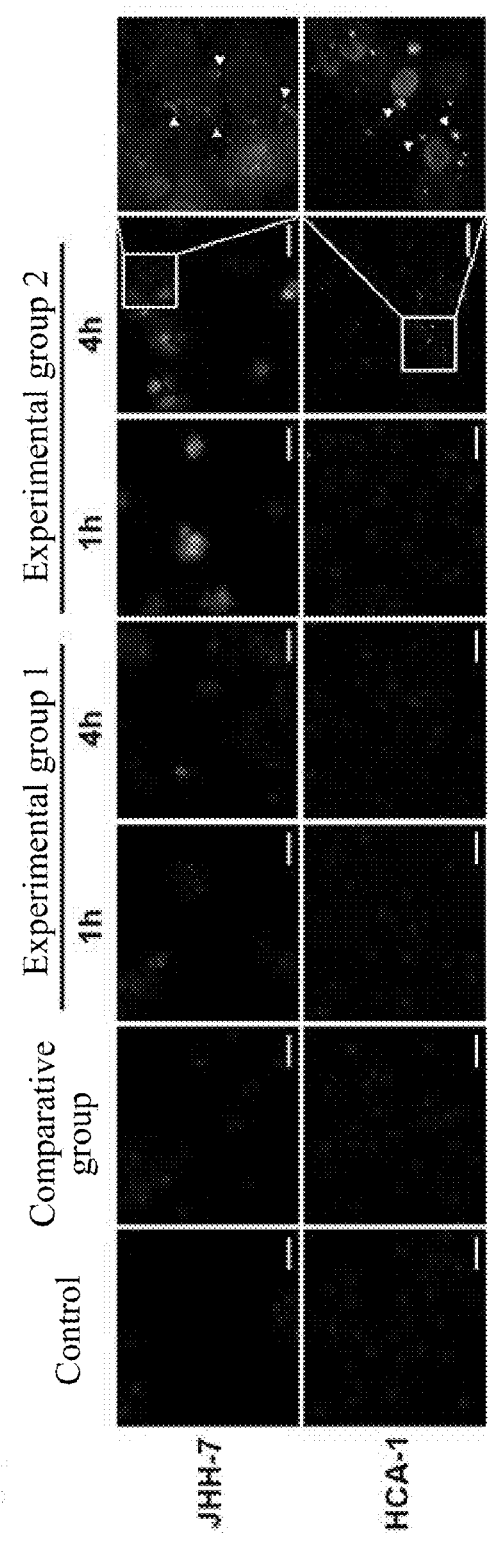
FIG. 8A, the fluorescence microscopy images of the accumulation of siRNA in JHH-7 cell and HCA-1 cell, the scale therein represents 50 µm.
Figure 8B:
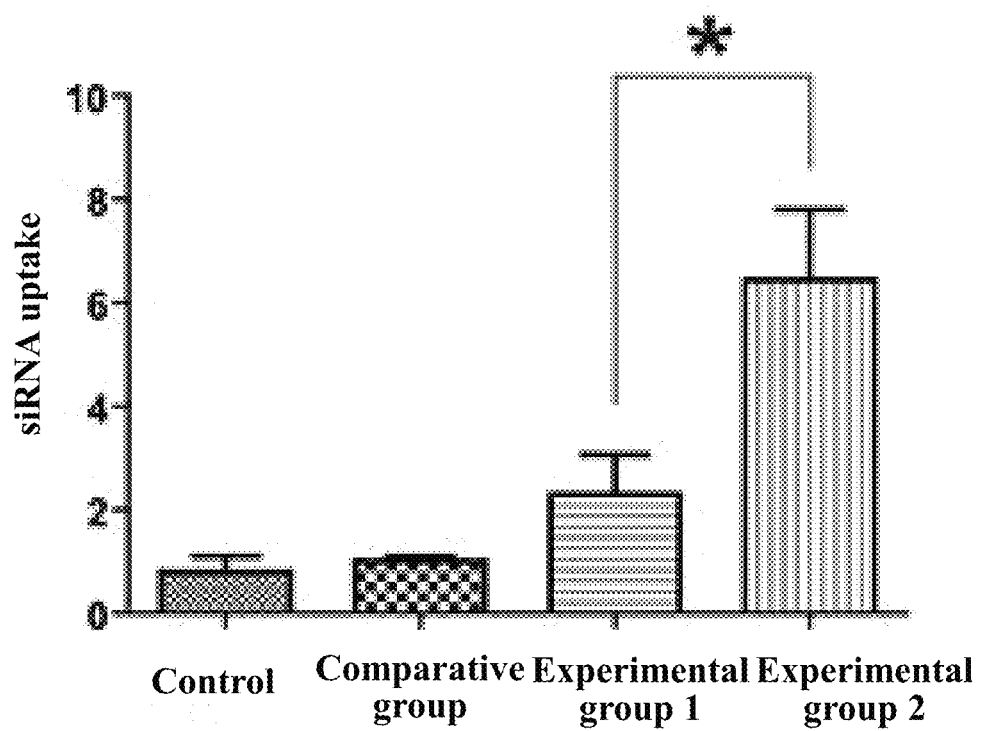
FIG. 8B, the accumulation of siRNA in JHH-7 cells, $*p<0.05$.
Figure 8C:
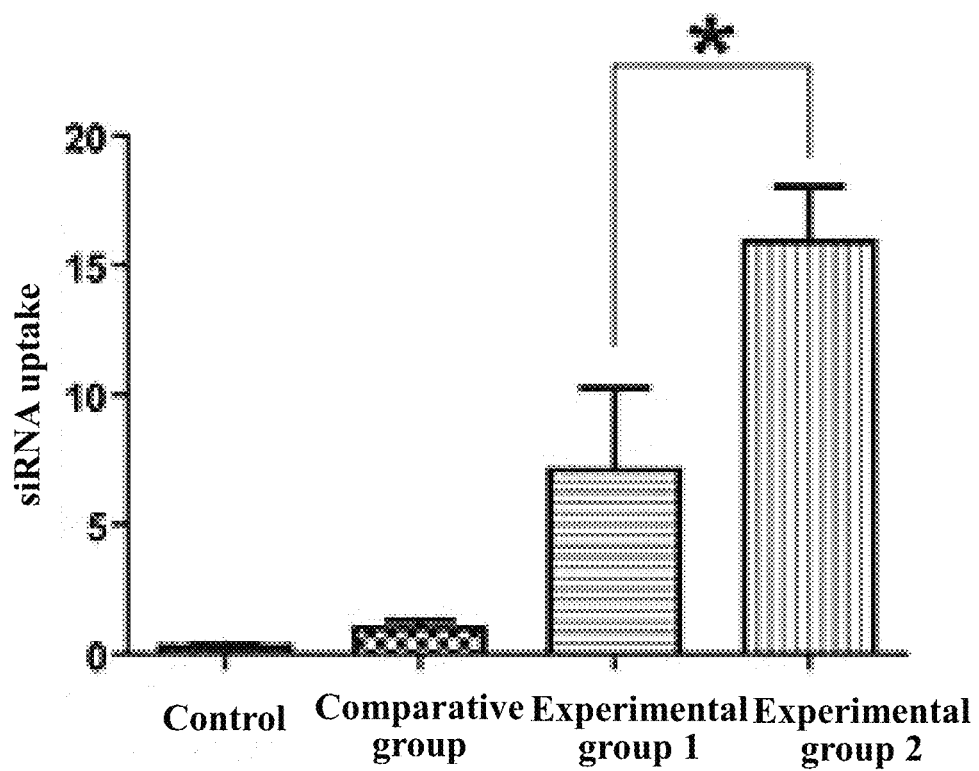
FIG. 8C, the accumulation of siRNA in HCA-1 cells, $*p<0.05$.
Figure 8D:
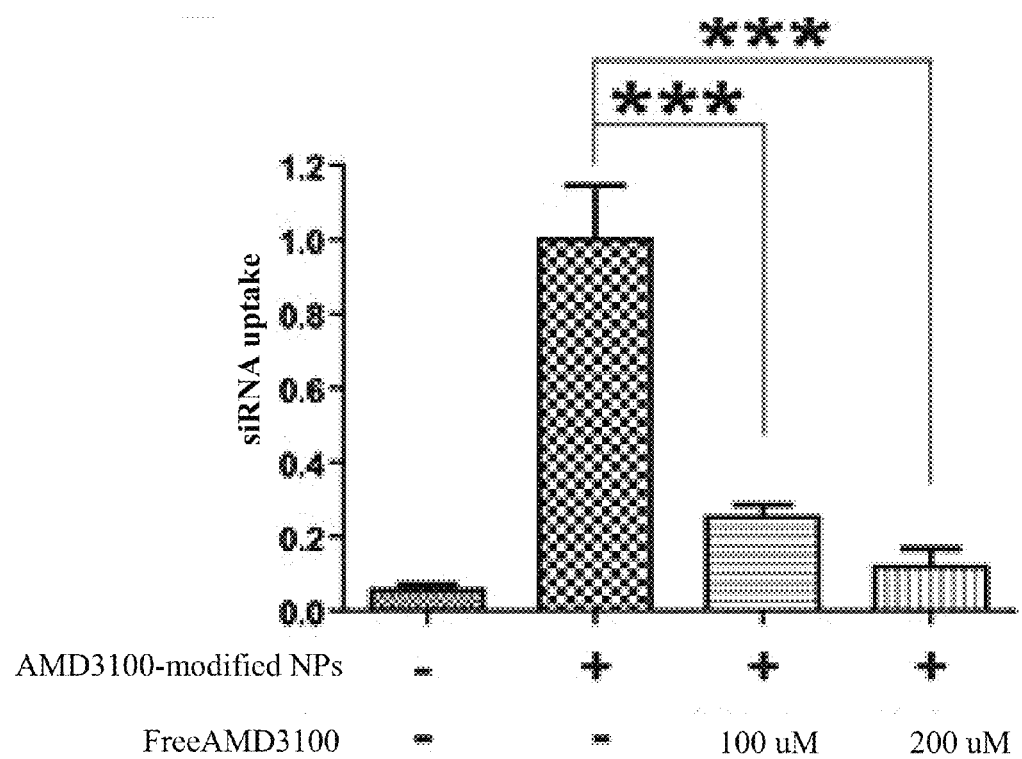
FIG. 8D, the accumulation of siRNA in HCA-1 cells treated with excessive amount of free AMD3100 as competitor, $***p<0.001$.
Figure 8E:
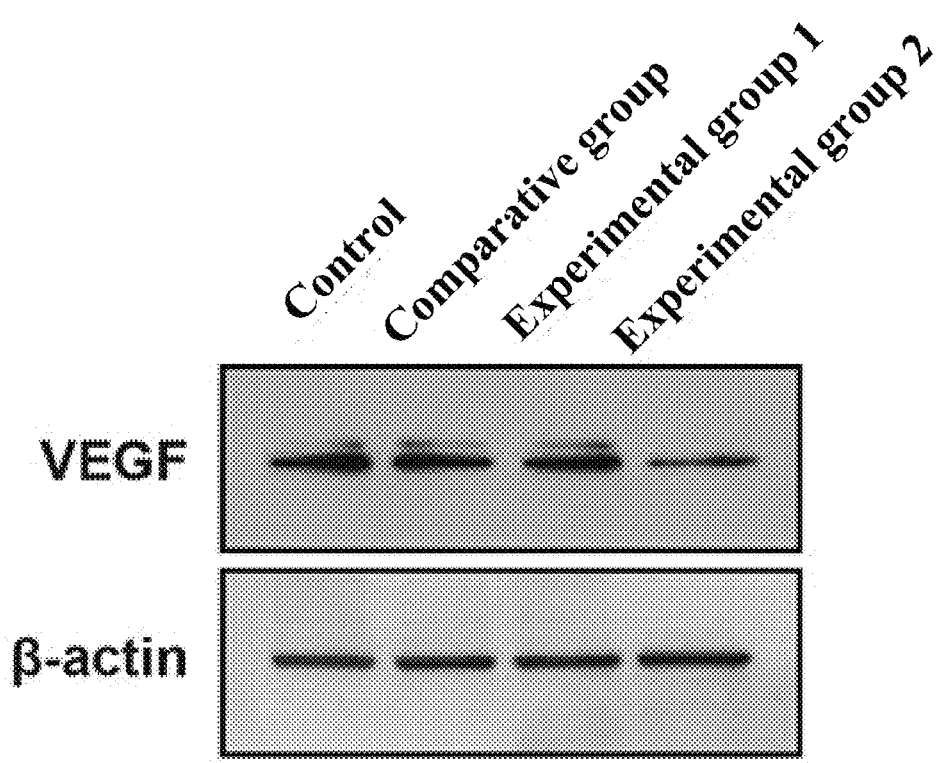
FIG. 8E, western blot of the gene expression of VEGF in JHH-7 cells.
Figure 8F:
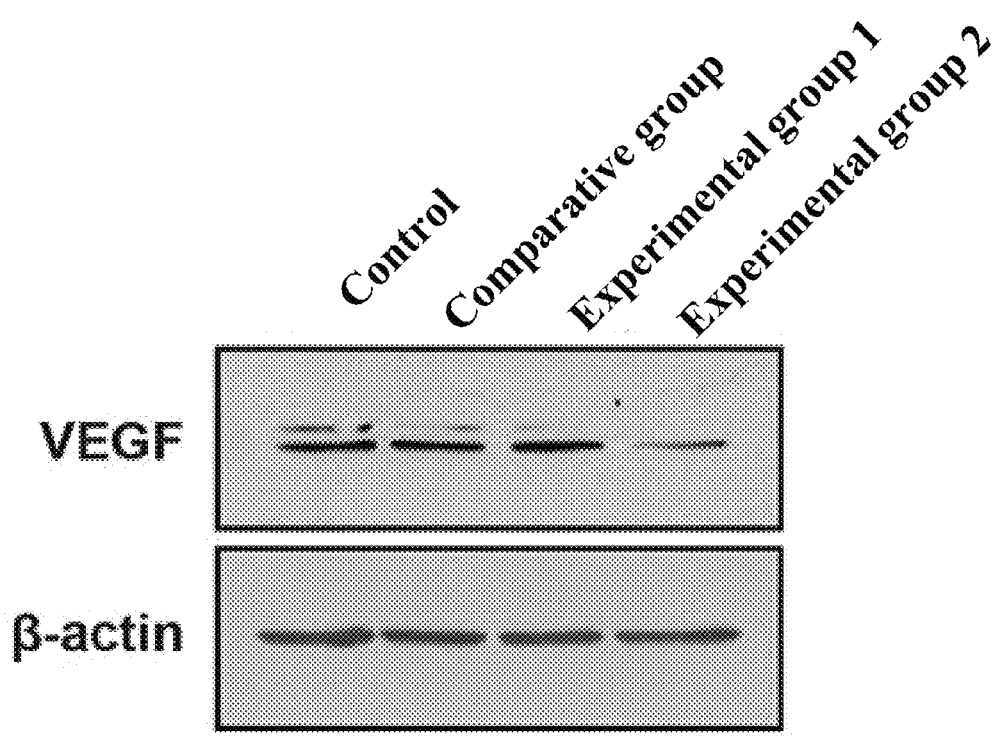
FIG. 8F, western blot of the gene expression of VEGF in HCA-1 cells.

As shown in FIG. 8A to FIG. 8C, for JHH-7 cells and HCA-1 cells, the uptake of the fluorescence-labeled siRNAs was much greater in Experimental group 2 compared with that of Experimental group 1. On the other hand, the uptake of anti-VEGF siRNA-loaded AMD3100-modified nanoparticle was competitively suppressed by the addition of free AMD3100 in a dose-dependent manner (FIG. 8D). Besides, for JHH-7 cells and HCA-1 cells, the Experimental group 2 showed significant suppression of VEGF expression, whereas no suppression of VEGF expression was observed in the Comparative group or the Experimental group 2, indicating that the AMD3100-modified lipid-coated nanoparticle efficiently deliver the nucleotide having an anti-angiogenic effect into CXCR4-expressing HCC cells and achieved a significant gene silencing effect. Both the delivery and silencing activity were ligand (AMD3100) dependent.

Figure 9A:
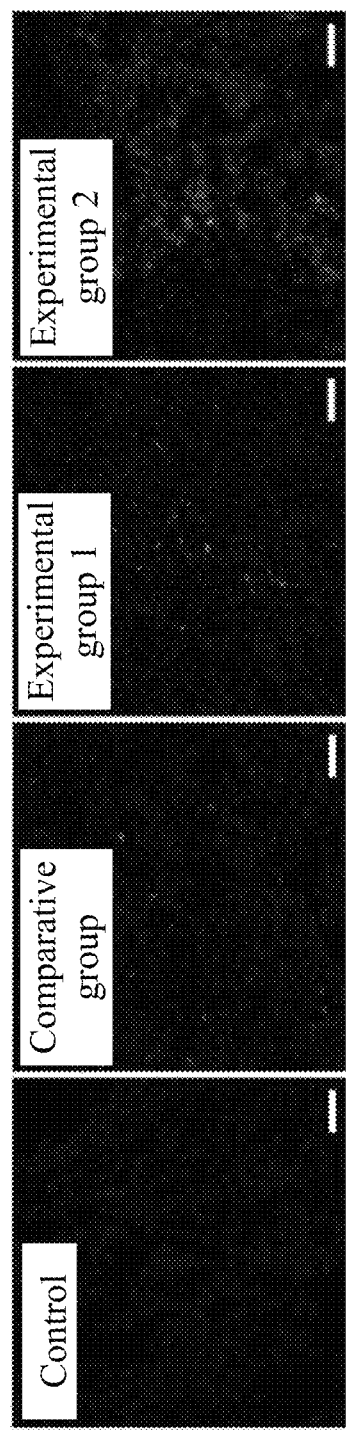
FIG. 9A, the fluorescence microscopy images of the accumulation of siRNA in the mice with orthotopic HCA-1 tumor, the scale therein represents 50 µm.
Figure 9B:
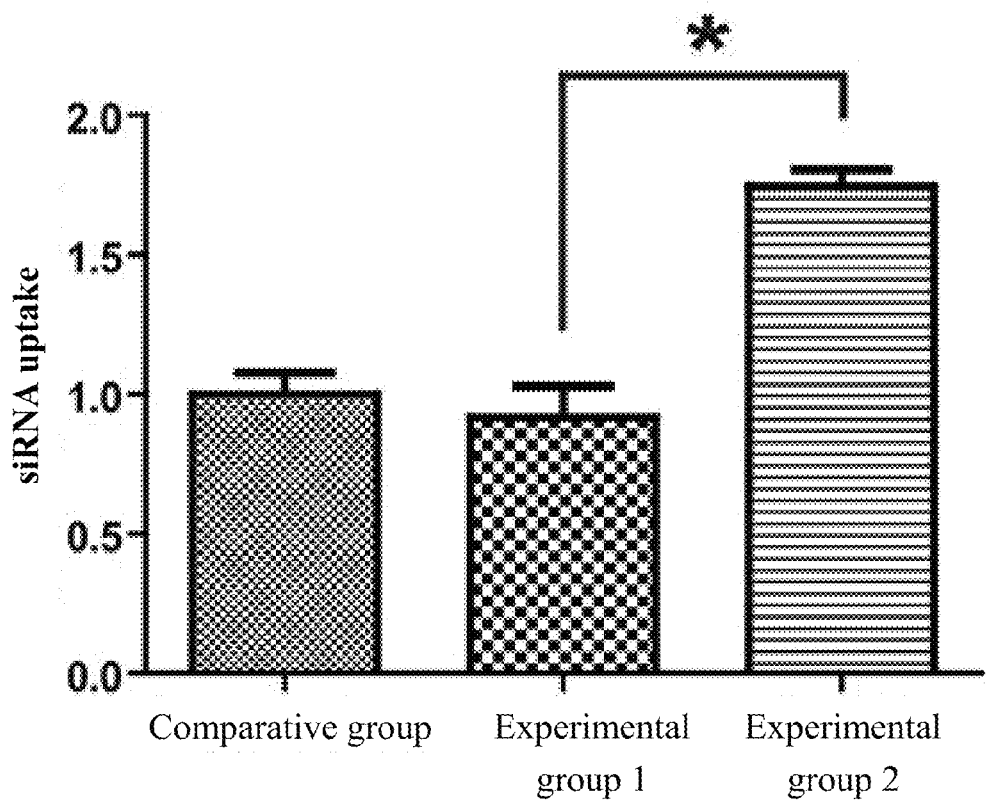
FIG. 9B, the accumulation of siRNA in the mice with orthotopic HCA-1 tumor, $*p<0.05$.
Figure 9C:
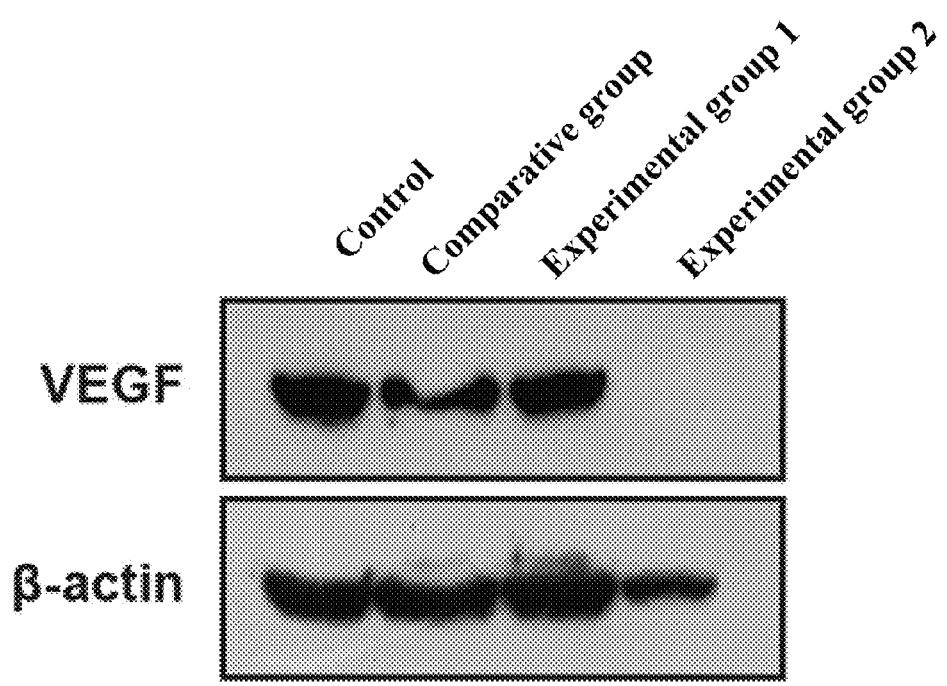
FIG. 9C, western blot of the gene expression of VEGF in the mice with orthotopic HCA-1 tumor.

Next, the uptake of the fluorescence-labeled siRNA in orthotopic HCA-1 tumor models via intravenous injection was evaluated after 4 hours. As shown in FIG. 9A and FIG. 9B, intensive cytosolic delivery and heterogeneous distribution of fluorescence-labeled siRNAs were observed for the Experimental group 2, indicating that the AMD3100-modified nanoparticle of the present invention can effectively deliver siRNA to orthotopic HCA-1 tumor. On the other hand, intracellular uptake can hardly be detected for both the Comparative group and the Experimental group 1. Furthermore, as shown in FIG. 9C, the VEGF expression in HCA-1 tumor was significantly suppressed when mice were treated with the siRNA-loaded AMD3100-modified nanoparticle, whereas no inhibitory effect was shown when mice were treated with siRNA-loaded nanoparticle without AMD3100 modification. It was noted that, according to FIG. 9C, the AMD3100-modified nanoparticle carrying non-therapeutic control siR- NAs also showed a moderate downregulation of VEGF expression in HCA-1 tumor tissues, suggesting that the SDF1α/CXCR4 axis was involved in regulating the expression of VEGF in HCC.

Moreover, effects of anti-VEGF siRNA-loaded AMD3100-modified nanoparticle on mean vessel density (MVD), hypoxic induction, SDF1α expression and TAM infiltration in HCA-1 transplanted HCC models were evaluated. Firstly, mice without any treatment were defined as Negative control group, while mice treated with free sorafenib were defined as Positive control group. Mice treated with control siRNA-loaded AMD3100-modified lipid-coated nanoparticle were defined as Comparative group. For the experimental groups, mice treated with anti-VEGF siRNA-loaded lipid-coated nanoparticle without AMD3100 modification were defined as Experimental group 1, while mice treated with anti-VEGF siRNA-loaded AMD3100-modified lipid-coated nanoparticle were defined as Experimental group 2.

Figure 10A:
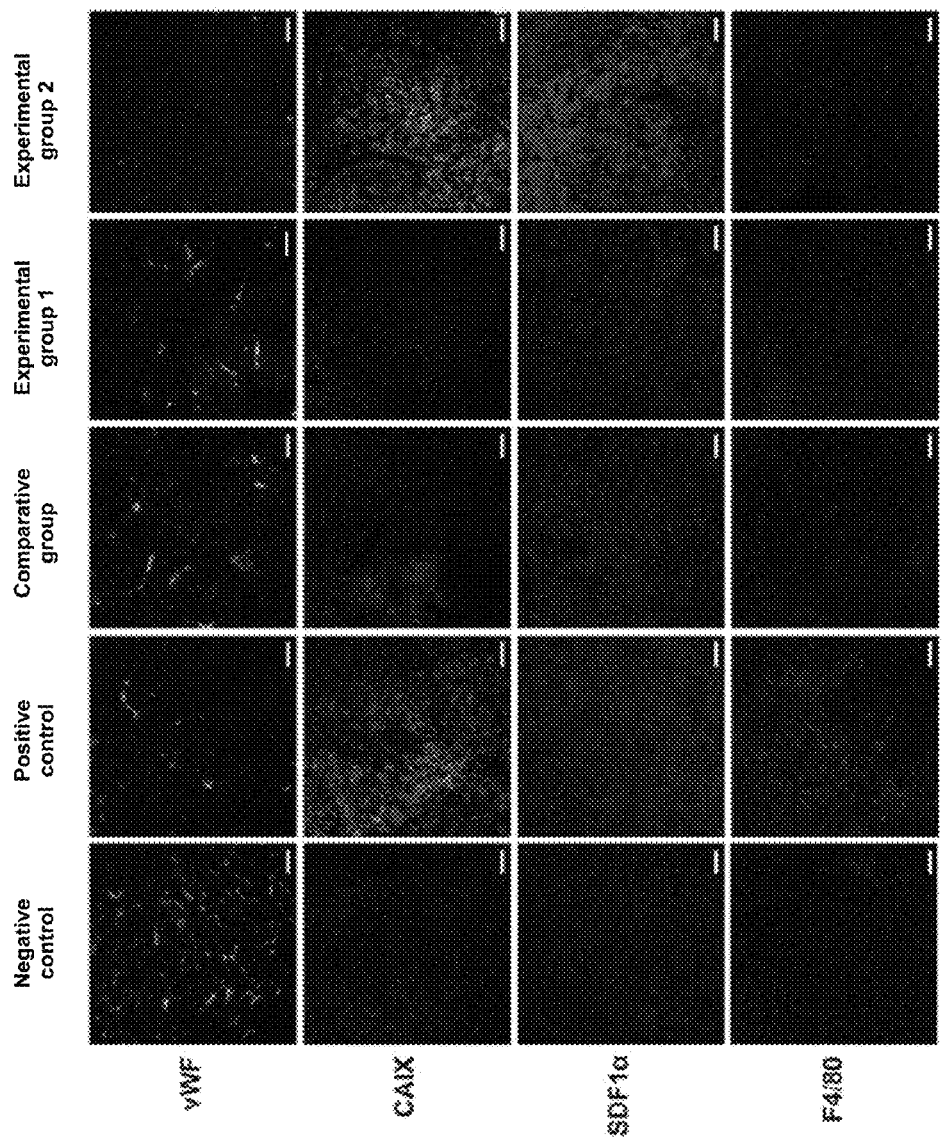
FIG. 10A, the fluorescence microscopy images of the mice with orthotopic HCA-1 tumor treated with the anti-VEGF siRNA-loaded AMD3100-modified lipid-coated nanoparticle of the present invention, the scale therein represents 50 µm.
Figure 10B:
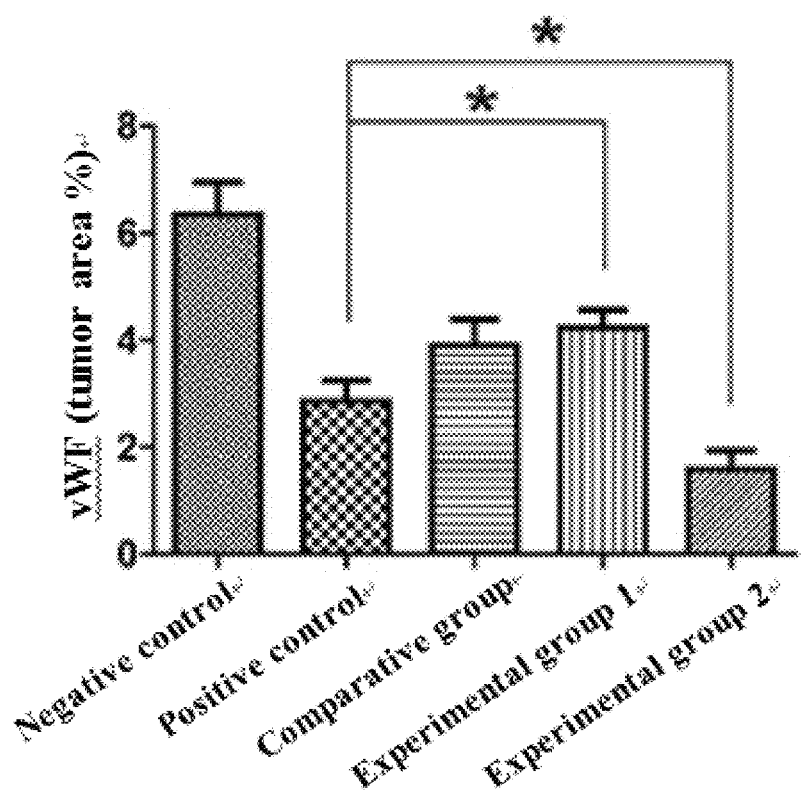
FIG. 10B, the quantification of the fluorescence microscopy images of the vWF factor expression in the mice with orthotopic HCA-1 tumor and treated with the anti-VEGF siRNA-loaded AMD3100-modified lipid-coated nanoparticle of the present invention, $*p<0.05$.
Figure 10C:
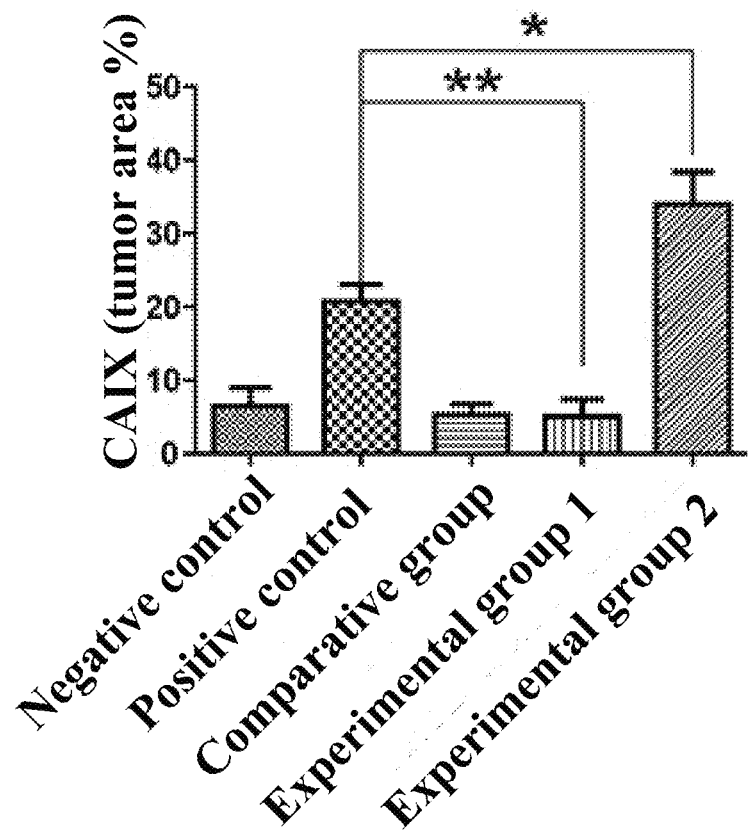
FIG. 10C, the quantification of the fluorescence microscopy images of the CAIX expression in the mice with orthotopic HCA-1 tumor and treated with the anti-VEGF siRNA-loaded AMD3100-modified lipid-coated nanoparticle of the present invention, $*p<0.05$, $**p<0.01$.
Figure 10D:
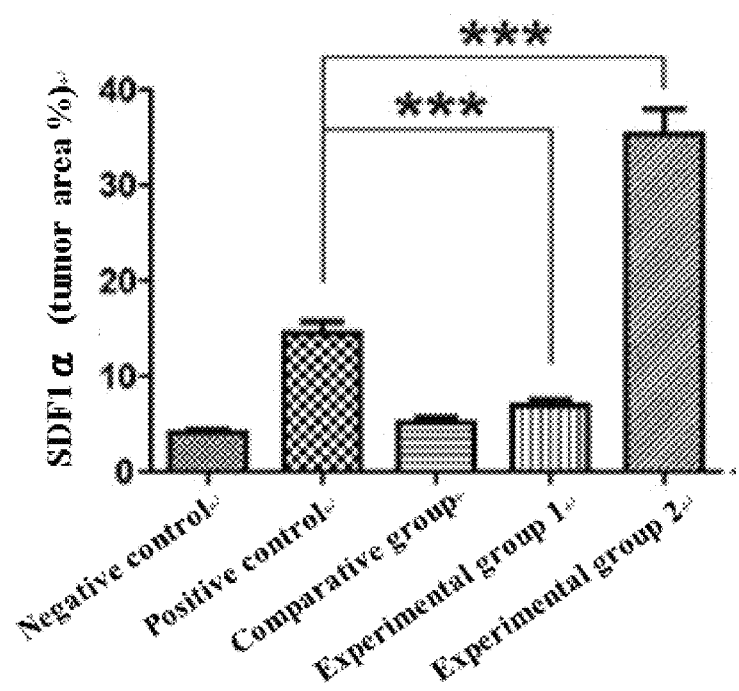
FIG. 10D, the quantification of the fluorescence microscopy images of the SDF1α expression in the mice with orthotopic HCA-1 tumor and treated with the anti-VEGF siRNA-loaded AMD3100-modified lipid-coated nanoparticle of the present invention, $***p<0.001$.
Figure 10E:
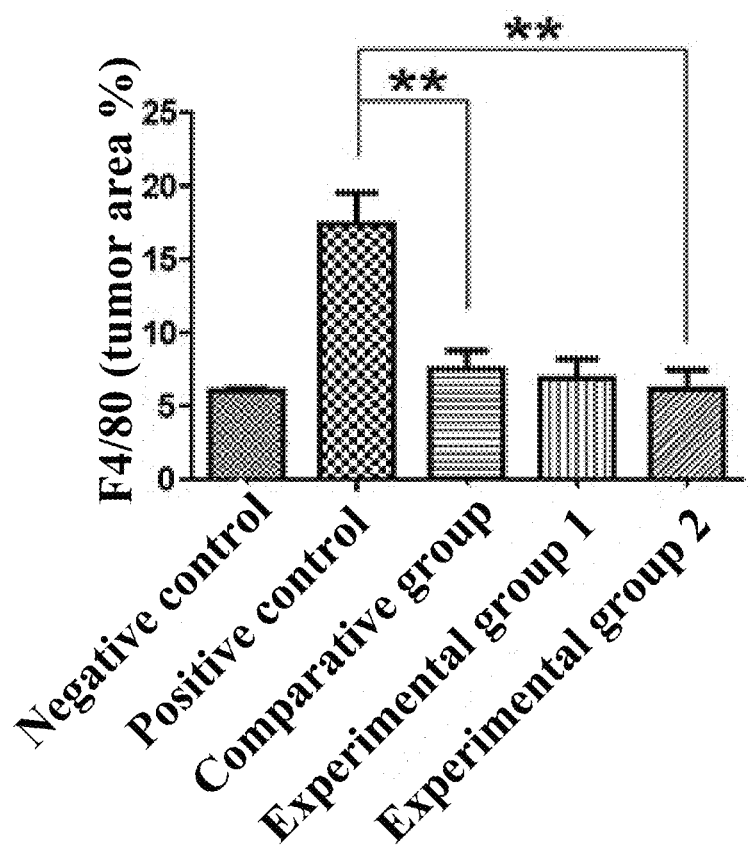
FIG. 10E, the quantification of the fluorescence microscopy images of tumor-associated macrophage F4/80 in the mice with orthotopic HCA-1 tumor treated with the anti-VEGF siRNA-loaded AMD3100-modified lipid-coated nanoparticle of the present invention, $**p<0.01$.

Mice with orthotopic HCA-1 tumor administrated via intravenous injection corresponded to the above mentioned Positive control group, Comparative group, Experimental group 1, and Experimental group 2. Comparing with the Experimental group 1 or the Comparative group, the Experimental group 2 showed significant reduction of MVD and noticeable increase of hypoxic fraction and SDF1α expression (FIG. 10A to FIG. 10D). The Experimental group 2 also showed a better inhibitory effect of angiogenesis than the Positive control group. On the other hand, despite the observation of increased hypoxic tissue fraction and SDF1α expression in the tumor tissues after treatment with anti-VEGF siRNA-loaded AMD3100-modified nanoparticles of the present invention (Experimental group 2), the infiltration of F4/80+ macrophages into the tumor tissues was not observed (FIG. 10A and FIG. 10E), indicating that the incorporation of AMD3100 into the anti-VEGF siRNA-loaded nanoparticles of the present invention can block the recruitment of TAMs into the tumor microenvironment.

Figure 11A:
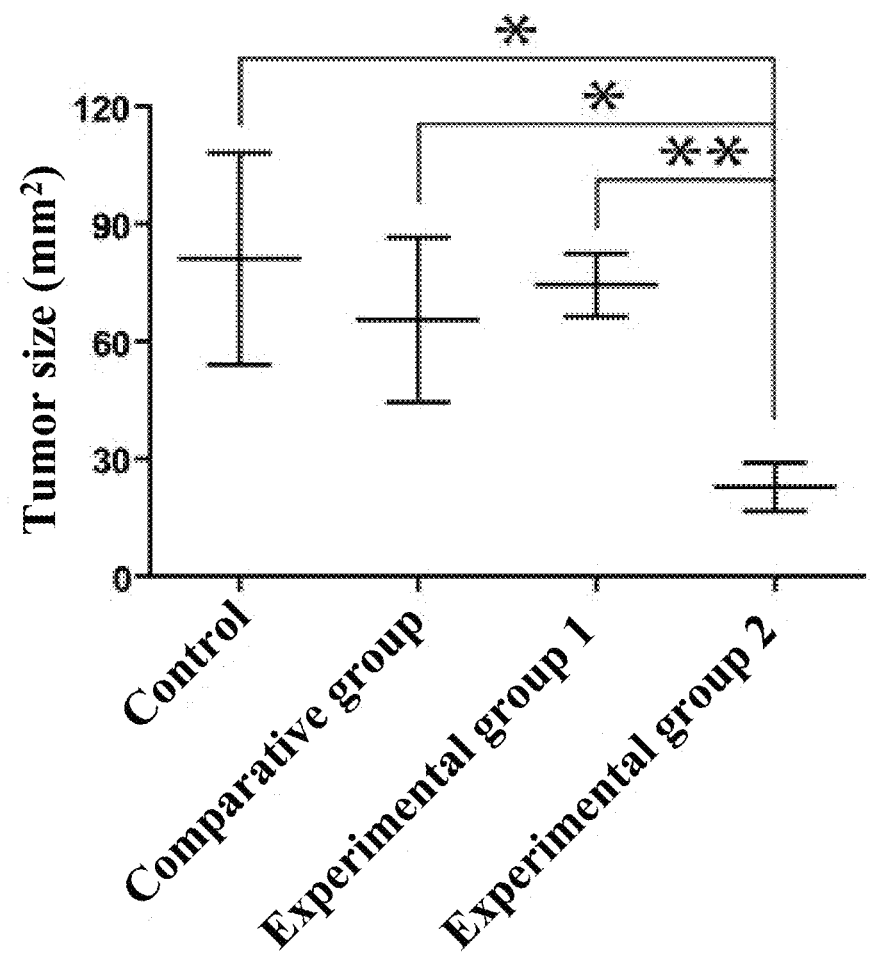
FIG. 11A, the tumor sizes of the mice with orthotopic HCA-1 tumor treated with anti-VEGF siRNA-loaded AMD3100-modified lipid-coated nanoparticle of the present invention, $*p<0.05$, $**p<0.01$.
Figure 11B:
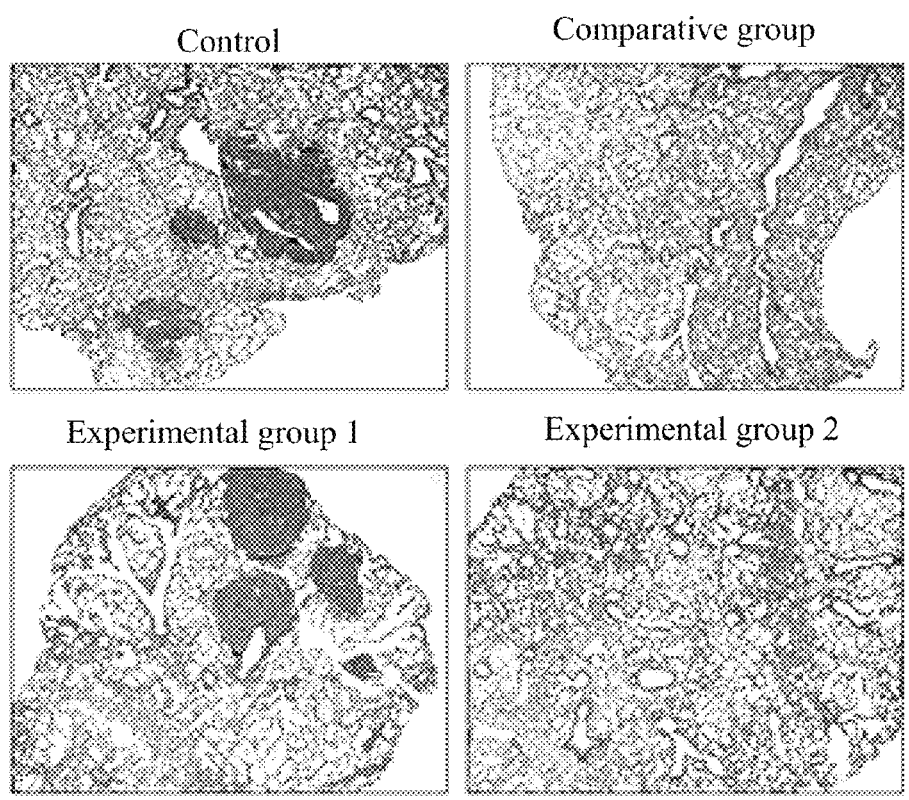
FIG. 11B, the microscopic images of the lung metastasis of the mice with orthotopic HCA-1 tumor treated with anti-VEGF siRNA-loaded AMD3100-modified lipid-coated nanoparticle of the present invention.
Figure 11C:
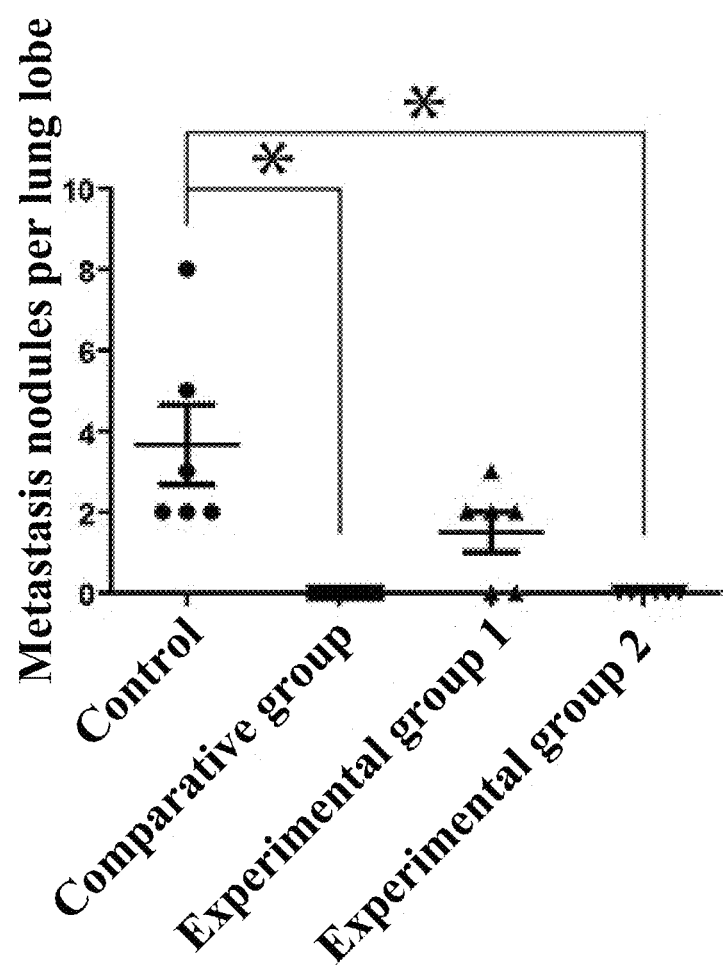
FIG. 11C, lung metastasis of the mice with orthotopic HCA-1 tumor treated with anti-VEGF siRNA-loaded AMD3100-modified lipid-coated nanoparticle of the present invention, $*p<0.05$.

Additionally, as shown in FIG. 11A, a delay in tumor growth of mice with orthotopic HCA-1 tumor was observed in the Experimental group 2. Since the in vitro study only showed a minor effect of treatment with anti-VEGF siRNA-loaded AMD3100-modified nanoparticle of the present invention on HCC viability, the suppression of HCC progression induced by the anti-VEGF siRNA-loaded AMD3100-modified nanoparticle of the present invention was mainly mediated by the tumor stroma. No significant suppression of tumor growth was observed for the Comparative group and the Experimental group 1, indicating that with AMD3100 modification, the anti-VEGF siRNA-loaded nanoparticle of the present invention enhance the effect of HCC suppression. However, it was also noted that, for mice model with orthotopic HCA-1 tumor, the Experimental group 2 or the Comparative group showed significant inhibitory activity regarding lung metastasis (FIG. 11B to FIG. 11C), suggesting that the AMD3100-modified lipid-coated nanoparticle of the present invention can antagonize CXCR4; thus effectively reduce metastasis.

In summary, the CXCR4-targeted lipid-coated nanoparticle encapsulating sorafenib or anti-VEGF siRNA of the present invention can be formulated into an injection due to its low polydispersity as well as good pharmacokinetics and blood circulation stability. The utilization of AMD3100 as the CXCR4-targeted molecule for modification of nanoparticle not only promotes specific targeted delivery, which the accumulation of sorafenib or anti-VEGF siRNA in target tissue is increased, but also effectively produces a synergistic therapeutic effect. Furthermore, the CXCR4-targeted lipid-coated nanoparticle encapsulating sorafenib or anti-VEGF siRNA of the present invention can also suppress tumor growth and metastasis of HCC.

The method for treatment of liver cancer and inhibition of metastasis according to the present invention are applicable and valuable to the industry. Those embodiments above are better results, and should not, however, be considered to limit the scope of the invention, it is contemplated that modifications will readily occur to those skilled in the art, which modifications will be within the spirit of the invention and scope of the appended claims.

What is claimed is:

1. A method for treatment of liver cancer and inhibition of metastasis of liver cancer, comprising administrating to a subject in need a therapeutically effective amount of a pharmaceutical composition comprising a CXC-chemokine-receptor 4(CXCR4)-targeted nanoparticle, the nanoparticle comprises:
   a core comprising an anti-angiogenesis drug or a nucleotide having an anti-angiogenic effect;
   a lipid carrier encapsulating the core; and
   a CXCR4-targeted molecule attached to the surface of the lipid carrier,
   wherein the CXCR4-targeted molecule specifically delivers the nanoparticle to a hepatocellular carcinoma and sensitizes the hepatocellular carcinoma to the anti-angiogenesis drug or nucleotide having an anti-angiogenic effect to provide a synergistic effect of the anti-angiogenesis drug or the nucleotide having the anti-angiogenic effect to the hepatocellular carcinoma.

2. The method of claim 1, wherein the lipid carrier further comprises a polymer, the polymer is poly [D, L-lactide-co-glycolide] (PLGA).

3. The method of claim 1, wherein the nanoparticle decreases the viability of the hepatocellular carcinoma.

4. The method of claim 2, wherein the nanoparticle decreases the viability of the hepatocellular carcinoma.

5. The method of claim 1, wherein the nanoparticle enhances the accumulation of the anti-angiogenesis drug or the nucleotide having the anti-angiogenic effect in the hepatocellular carcinoma.

6. The method of claim 2, wherein the nanoparticle enhances the accumulation of the anti-angiogenesis drug or the nucleotide having the anti-angiogenic effect in the hepatocellular carcinoma.

7. The method of claim 1, wherein the nanoparticle further decreases the density and diameter of a new vessel of the hepatocellular carcinoma.

8. The method of claim 2, wherein the nanoparticle further decreases the density and diameter of a new vessel of the hepatocellular carcinoma.

9. The method of claim 1, wherein the nanoparticle further comprises a stabilizer.

10. The method of claim 2, wherein the nanoparticle further comprises an emulsifier.

11. The method of claim 9, wherein the stabilizer is 1,2-distearoyl-sn-glycero-3-phosphoethanolamine-N-[amino (polyethylene glycol)-2000] (DSPE-PEG(2000)).

12. The method of claim 10, wherein the emulsifier is D-α-Tocopherol polyethylene glycol 1000 succinate (TPGS).

13. The method of claim 2, wherein the anti-angiogenesis drug is sorafenib.

14. The method of claim 1, wherein the nucleotide having the anti-angiogenic effect is a small interfering RNA (siRNA).

15. The method of claim 2, wherein the CXCR4-targeted molecule is a CXCR4 anatognist.

16. The method of claim 15, wherein the CXCR4 anatognist is AMD3100.

17. The method of claim 16, wherein the AMD3100 increases the sensitivity of the hepatocellular carcinoma to the anti-angiogenesis drug and the nucleotide having the anti-angiogenic effect.

18. The method of claim 1, wherein the pharmaceutical composition is an injection.

19. The method of claim 2, wherein the pharmaceutical composition is an injection.

\* \* \* \* \*